United States Patent
Guo et al.

(10) Patent No.: US 12,106,489 B2
(45) Date of Patent: Oct. 1, 2024

(54) SYSTEMS AND METHODS FOR DETERMINING HEMODYNAMIC PARAMETERS

(71) Applicant: SHANGHAI UNITED IMAGING HEALTHCARE CO., LTD., Shanghai (CN)

(72) Inventors: Jian Guo, Shanghai (CN); Yuxiang Guo, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 211 days.

(21) Appl. No.: 17/929,680

(22) Filed: Sep. 2, 2022

(65) Prior Publication Data
US 2022/0414895 A1    Dec. 29, 2022

Related U.S. Application Data

(63) Continuation of application No. PCT/CN2020/142228, filed on Dec. 31, 2020.

(30) Foreign Application Priority Data

Mar. 3, 2020    (CN) .......................... 202010138437.7

(51) Int. Cl.
*G06T 7/20*    (2017.01)
*A61B 8/06*    (2006.01)
(Continued)

(52) U.S. Cl.
CPC ................. *G06T 7/20* (2013.01); *A61B 8/06* (2013.01); *G06T 7/11* (2017.01); *G06T 7/149* (2017.01);
(Continued)

(58) Field of Classification Search
None
See application file for complete search history.

(56) References Cited

U.S. PATENT DOCUMENTS 7,620,501 B2    11/2009    Tek et al.
9,629,563 B2    4/2017    Sharma et al.
(Continued)

FOREIGN PATENT DOCUMENTS

CN    104794973 A    7/2015
CN    105096388 A    11/2015
(Continued)

OTHER PUBLICATIONS

International Search Report in PCT/CN2020/142228 mailed on Apr. 6, 2021, 5 pages.
(Continued)

*Primary Examiner* — Nurun Flora
(74) *Attorney, Agent, or Firm* — METIS IP LLC

(57) ABSTRACT

A method for determining hemodynamic parameters may be provided. The method may include obtaining image data of a subject. The method may include generating a first vascular model and a second vascular model based on the image data and coupling the first vascular model with the second vascular model using an intermediate model to form a coupled vascular model. The method may also include setting at least one of a first boundary condition of the first vascular model or a second boundary condition of the second vascular model and determining a flow field distribution of the coupled vascular model based on the at least one of the first boundary condition or the second boundary condition. The method may further include determining hemodynamic parameters based on the flow field distribution.

20 Claims, 9 Drawing Sheets

(51) Int. Cl.
  *G06T 7/11* (2017.01)
  *G06T 7/149* (2017.01)
  *G06T 17/20* (2006.01)
  *G06V 10/44* (2022.01)

(52) U.S. Cl.
  CPC .............. *G06T 17/20* (2013.01); *G06V 10/44* (2022.01); *G06T 2207/10132* (2013.01); *G06T 2207/30104* (2013.01)

(56) References Cited

U.S. PATENT DOCUMENTS

| | | |
|---|---|---|
| 2011/0104651 A1 | 5/2011 | Sweeney |
| 2013/0132054 A1 | 5/2013 | Sharma et al. |
| 2018/0211388 A1* | 7/2018 | Ma .................. G16H 50/50 |
| 2018/0242856 A1 | 8/2018 | Onozawa et al. |
| 2020/0037982 A1 | 2/2020 | Van Der Horst et al. |

FOREIGN PATENT DOCUMENTS

| | | |
|---|---|---|
| CN | 106780477 A | 5/2017 |
| CN | 108597613 A | 9/2018 |
| CN | 110457765 A | 11/2019 |
| WO | 2014107769 A1 | 7/2014 |
| WO | 2021174992 A1 | 9/2021 |

OTHER PUBLICATIONS

Written Opinion in PCT/CN2020/142228 mailed on Apr. 6, 2021, 5 pages.

First Office Action in Chinese Application No. 202010138437.7 mailed on Feb. 20, 2021, 23 pages.

The Second Office Action in Chinese Application No. 202010138437.7 mailed on Jul. 16, 2021, 21 pages.

Roberto J. Groszmann et al., Wedged and Free Hepatic Venous Pressure Measured with a Balloon Catheter, Gastroenterology, 76(2): 253-258, 1979.

Roberto J. Groszmann et al., The Hepatic Venous Pressure Gradient: Anything Worth Doing Should Be Done Right, Hepatology, 39(2): 280-282, 2004.

Roberto De Franchis, Evolving Consensus in Portal Hypertension Report of the Baveno IV Consensus Workshop on Methodology of Diagnosis and Therapy in Portal Hypertension, Journal of Hepatology, 43(1): 167-178, 2005.

Guadalupe Garcia-Tsao et al., Management of Varices and Variceal Hemorrhage in Cirrhosis, The New England Journal of Medicine, 362(9): 823-832, 2010.

Roberto De Franchis, Expanding Consensus in Portal Hypertension Report of the Baveno VI Consensus Workshop: Stratifying Risk and Individualizing Care for Portal Hypertension, Journal of Hepatology, 63(3): 743-752, 2015.

James K. Min et al., Diagnostic Accuracy of Fractional Flow Reserve From Anatomic CT Angiography, JAMA, 308(12): 1237-1245, 2012.

Michael T. Lu et al., Noninvasive FFR Derived From Coronary CT Angiography: Management and Outcomes in the PROMISE Trial, JACC: Cardiovasc Imaging, 10(11): 1350-1358, 2017.

A. Sboarina et al. Software for Hepatic Vessel Classification: Feasibility Study for Virtual Surgery, International Journal of Computer Assisted Radiology and Surgery, 5(1): 39-48, 2010.

Mette S. Olufsen, Structured Tree Outflow Condition for Blood Flow in Larger Systemic Arteries, The American Physiological Society, 276(1): H257-H268, 1999.

\* cited by examiner

SYSTEMS AND METHODS FOR DETERMINING HEMODYNAMIC PARAMETERS

CROSS-REFERENCE TO RELATED APPLICATIONS

This application is a continuation of International Application No. PCT/CN2020/142228, filed on Dec. 31, 2020, which claims priority to Chinese Patent Application No. 2020101384377, filed on Mar. 3, 2020, the content of which are hereby incorporated by reference.

TECHNICAL FIELD

The present disclosure generally relates to fluid dynamics, and more particularly, to a method and system for determining hemodynamic parameters of a subject.

BACKGROUND

Hemodynamic parameter analysis is widely used for diagnoses of a vascular disease or vasculature of a lesion such as vascular stenosis (e.g., vertebral artery stenosis), aneurysm, dissecting aneurysm, cancer, a tumor-feeding artery, etc. Generally, hemodynamic parameters of a subject (e.g., a patient) are determined based on invasive measurements or non-invasive measurements. However, the invasive measurements may cause physical damages to the subject and bring about various risks, while conventional non-invasive measurements have a low accuracy. Thus, it is desirable to develop a system and method for determining hemodynamic parameters of the subject more accurately and efficiently.

SUMMARY

According to an aspect of the present disclosure, a method implemented on a computing device having a processor and a computer-readable storage device may be provided. The method may include obtaining image data of a subject. The subject may include at least one first blood vessel and at least one second blood vessel. The at least one first blood vessel and at least one second blood vessel may constitute a blood flow path. The method may include generating a first vascular model and a second vascular model based on the image data of the subject. The first vascular model and the second vascular model may correspond to the at least one first blood vessel and the at least one second blood vessel, respectively. The method may include coupling the first vascular model with the second vascular model using an intermediate model. The first vascular model, the second vascular model, and the intermediate model may form a coupled vascular model. The method may also include setting at least one of a first boundary condition of the first vascular model or a second boundary condition of the second vascular model. The method may further include determining a flow field distribution of the coupled vascular model based on the at least one of the first boundary condition of the first vascular model or the second boundary condition of the second vascular model. The method may further include determining at least one of a value of a first hemodynamic parameter of the at least one first blood vessel or a value of a second hemodynamic parameter of the at least one second blood vessel based on the flow field distribution of the coupled vascular model.

In some embodiments, the image data of the subject may correspond to at least two time phases of the subject.

In some embodiments, to generate a first vascular model and a second vascular model based on the image data of the subject, the method may include segmenting the at least one first blood vessel and at least one second blood vessel from the image data of the subject. The method may also include extracting features of the segmented at least one first blood vessel and at least one second blood vessel. The method may further include generating the first vascular model and the second vascular model based on the extracted features.

In some embodiments, the first vascular model may include at least one first bifurcation end, and the second vascular model may include at least one second bifurcation end. To couple the first vascular model with the second vascular model using an intermediate model, the method may include determining a correspondence relationship between the at least one first bifurcation end and the at least one second bifurcation end. The method may also include determining one or more bifurcation end pairs based on the correspondence relationship. Each of the one or more bifurcation end pairs may include a first bifurcation end and a corresponding second bifurcation end. The method may further include connecting the first bifurcation end and the corresponding second bifurcation end of each of the one or more bifurcation end pairs via a flow resistance model of the intermediate model.

In some embodiments, the flow resistance model may be a zero-dimensional model.

In some embodiments, to set at least one of a first boundary condition of the first vascular model or a second boundary condition of the second vascular model, the method may include setting the first boundary condition of the first vascular model. The first boundary condition may include at least one of a first entrance flow velocity, a first entrance blood mass flow rate, or a first entrance reference pressure at an entrance of the at least one first blood vessel, or a first exit flow velocity, a first exit blood mass flow rate, or a first exit reference pressure at an exit of the at least one first blood vessel.

In some embodiments, the first entrance flow velocity may be measured using an ultrasonic detector.

In some embodiments, to determine a flow field distribution of the coupled vascular model based on the at least one of the first boundary condition of the first vascular model or the second boundary condition of the second vascular model, the method may include generating a meshed coupled vascular model by gridding the coupled vascular model. The method may further include determining the flow field distribution of the coupled vascular model based on the meshed coupled vascular model and the first boundary condition.

In some embodiments, the meshed coupled vascular model may include a meshed first vascular model and a meshed second vascular model. To determine the flow field distribution of the coupled vascular model based on the meshed coupled vascular model and the first boundary condition, the method may include determining a first local flow field distribution of the meshed first vascular model based on the first boundary condition. The method may also include determining a second boundary condition of the second vascular model based on the intermediate model and the first local flow field distribution. The second boundary condition may include at least one of a second entrance flow velocity, a second entrance blood mass flow rate, or a second entrance reference pressure at an entrance of the at least one second blood vessel, or second exit flow velocity, a second exit blood mass flow rate or a second exit reference pressure at an exit of the at least one second blood vessel. The method may further include determining a second local flow field distribution of the meshed second vascular model based on the second boundary condition.

In some embodiments, to determine at least one of a value of a first hemodynamic parameter of the at least one first blood vessel or a value of a second hemodynamic parameter of the at least one second blood vessel based on the flow field distribution of the coupled vascular model, the method may include determining at least one of the value of the first hemodynamic parameter of the at least one first blood vessel based on the first local flow field distribution, or the value of the second hemodynamic parameter of the at least one second blood vessel based on the second local flow field distribution. The first hemodynamic parameter may include at least one of a pressure, a wall stress, a wall shear stress (WSS), or a flow velocity, at each of one or more positions of the at least a part of the at least one first blood vessel. The second hemodynamic parameter may include at least one of a pressure, a wall stress, a WSS, or a flow velocity, at each of one or more positions of the at least a part of the at least one second blood vessel.

In some embodiments, the at least one first blood vessel may include a first main blood vessel and at least one first branch blood vessel. The at least one second blood vessel may include a second main blood vessel and at least one second branch blood vessel. The method may further include determining a value of a pressure gradient between the first main blood vessel and the second main blood vessel.

In some embodiments, the at least one first blood vessel may include a portal vein. The at least one second blood vessel may include a hepatic vein.

According to another aspect of the present disclosure, a system may be provided. The system may include one or more storage devices and one or more processors configured to communicate with the one or more storage devices. The one or more storage devices may store executable instructions. When the one or more processors execute the executable instructions, the one or more processors may be directed to cause the system to perform one or more of the following operations. The system may obtain image data of a subject. The subject may include at least one first blood vessel and at least one second blood vessel. The at least one first blood vessel and at least one second blood vessel may constitute a blood flow path. The system may generate a first vascular model and a second vascular model based on the image data of the subject. The first vascular model and the second vascular model may correspond to the at least one first blood vessel and the at least one second blood vessel, respectively. The system may couple the first vascular model with the second vascular model using an intermediate model. The first vascular model, the second vascular model, and the intermediate model may form a coupled vascular model. The system may also set at least one of a first boundary condition of the first vascular model or a second boundary condition of the second vascular model. The system may further determine a flow field distribution of the coupled vascular model based on the at least one of the first boundary condition of the first vascular model or the second boundary condition of the second vascular model. The system may further determine at least one of a value of a first hemodynamic parameter of the at least one first blood vessel or a value of a second hemodynamic parameter of the at least one second blood vessel based on the flow field distribution of the coupled vascular model.

According to yet another aspect of the present disclosure, a non-transitory computer readable medium may be provided. The non-transitory computer readable may include at least one set of instructions. When executed by one or more processors of a computing device, the at least one set of instructions may cause the computing device to perform a method. The method may include obtaining image data of a subject. The subject may include at least one first blood vessel and at least one second blood vessel. The at least one first blood vessel and at least one second blood vessel may constitute a blood flow path. The method may include generating a first vascular model and a second vascular model based on the image data of the subject. The first vascular model and the second vascular model may correspond to the at least one first blood vessel and the at least one second blood vessel, respectively. The method may include coupling the first vascular model with the second vascular model using an intermediate model. The first vascular model, the second vascular model, and the intermediate model may form a coupled vascular model. The method may also include setting at least one of a first boundary condition of the first vascular model or a second boundary condition of the second vascular model. The method may further include determining a flow field distribution of the coupled vascular model based on the at least one of the first boundary condition of the first vascular model or the second boundary condition of the second vascular model. The method may further include determining at least one of a value of a first hemodynamic parameter of the at least one first blood vessel or a value of a second hemodynamic parameter of the at least one second blood vessel based on the flow field distribution of the coupled vascular model.

Some of appended features of the present disclosure are illustrated in the following description. The appended features of the present disclosure are obvious to those skilled in the art, under the teaching of the description with appended drawings or the productions/operations of the embodiments. The features of the present disclosure may be implemented and realized by the practice or use of various methods, means and combinations of various aspects of the embodiments described below.

BRIEF DESCRIPTION OF THE DRAWINGS

The present disclosure is further described in terms of schematic embodiments. These schematic embodiments are described in detail with reference to the drawings. The drawings are not to scale. These embodiments are non-limiting schematic embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Figure 2:
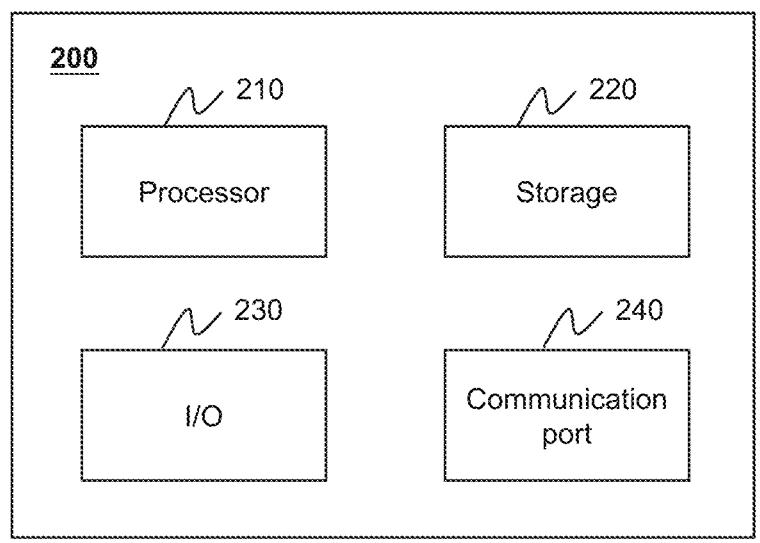
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and methods for non-invasive imaging, such as for disease diagnosis, treatment, and/or research purposes. In some embodiments, the blood vessel parameter determination system may include a single modality system and/or a multi-modality system. The term "modality" used herein broadly refers to an imaging or treatment method or technology that gathers, generates, processes, and/or analyzes imaging information of a subject or treatments the subject. The single modality system may include a computed tomography (CT) system, a magnetic resonance imaging (MRI) system, an ultrasound imaging system, an X-ray imaging system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include an X-ray imaging-magnetic resonance imaging (X-ray-MRI) system, a positron emission tomography-X-ray imaging (PET-X-ray) system, a single-photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, or the like, or any combination thereof.

In the present disclosure, the term "image" may refer to a two-dimensional (2D) image, a three-dimensional (3D) image, or a four-dimensional (4D) image. In some embodiments, the term "image" may refer to an image of a region (e.g., a region of interest (ROI)) of a subject. As described above, the image may be a CT image, a PET image, an MR image, a fluoroscopy image, an ultrasound image, an Electronic Portal Imaging Device (EPID) image, etc.

An aspect of the present disclosure relates to systems and methods for determining hemodynamic parameters. The system may generate a first vascular model and a second vascular model based on image data of a subject. The system may couple the first vascular model with the second vascular model using an intermediate model to form a coupled vascular model. The system may determine a flow field distribution of the coupled vascular model. The system may further determine a value of a hemodynamic parameter based on the flow field distribution of the coupled vascular model. In some embodiments, a hemodynamic parameter of a blood vessel may include a pressure, a wall stress, a wall shear stress (WSS), a flow velocity, etc., at each of one or more positions of the blood vessel. In some embodiments, the hemodynamic parameter of a blood vessel may include a mean value, a maximum value, a minimum value, a ratio, a difference, etc., of pressures, wall stresses, WSS's, and/or flow velocities at multiple positions of the blood vessel. By coupling the first vascular model with the second vascular model using the intermediate model (e.g., at least one flow resistance model), the value of the hemodynamic parameter of a blood vessel may be determined in a non-invasive, and the accuracy of the value of the hemodynamic parameter may be effectively improved.

Figure 1:
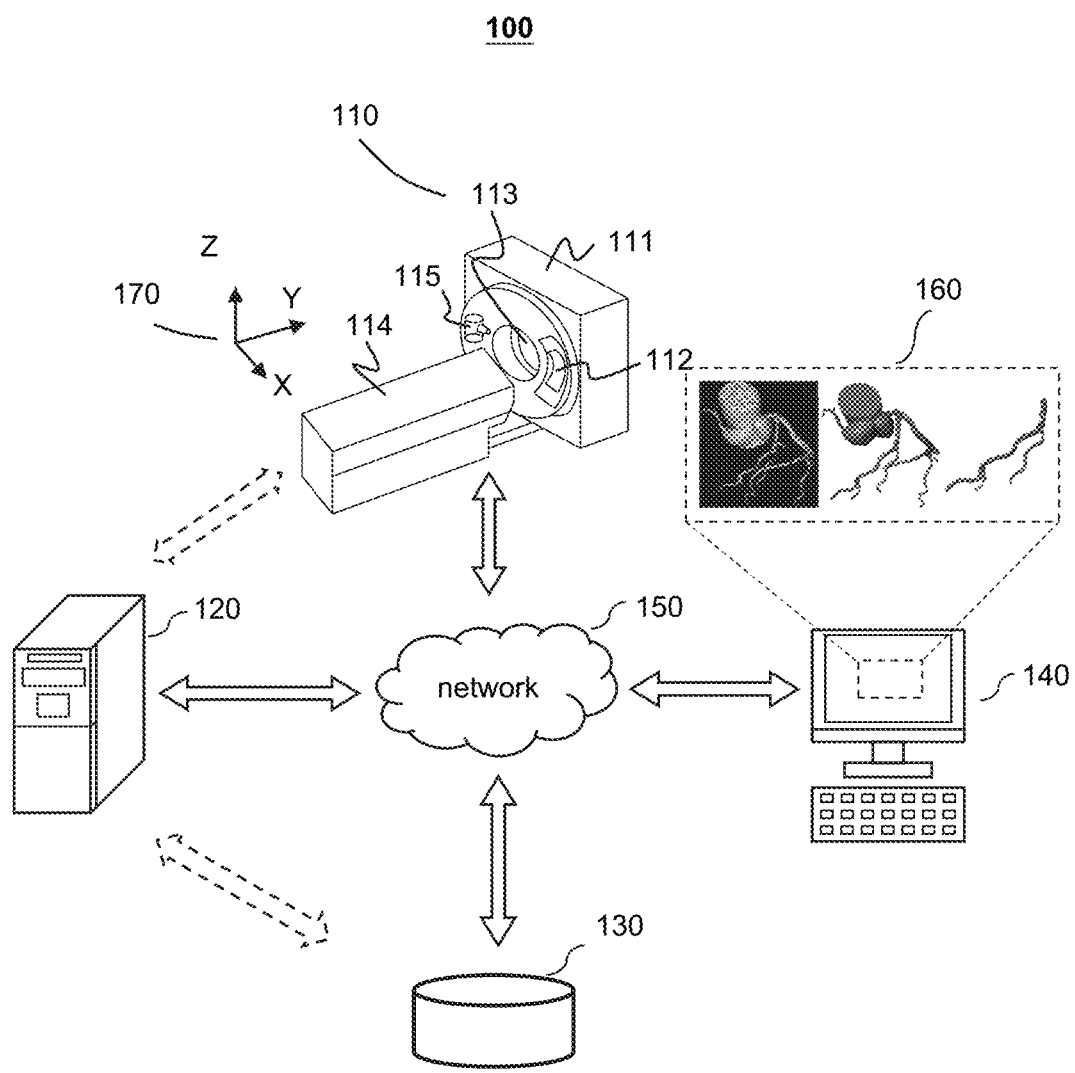
FIG. 1 is a schematic diagram illustrating an exemplary blood vessel parameter determination according to some embodiments of the present disclosure.

FIG. 1 is a schematic diagram illustrating an exemplary blood vessel parameter determination system according to some embodiments of the present disclosure. As illustrated in FIG. 1, the hemodynamic parameters determination system 100 may include a data acquisition device 110, a processing device 120, a storage device 130, a terminal device 140, and a network 150. In some embodiments, two or more components of the hemodynamic parameters determination system 100 may be connected to and/or communicate with each other via a wireless connection, a wired connection, or a combination thereof. The connection among the components of the hemodynamic parameters determination system 100 may be variable. Merely by way of example, the data acquisition device 110 may be connected to the processing device 120 through the network 150 or directly. As another example, the storage device 130 may be connected to the processing device 120 through the network 150 or directly.

The data acquisition device 110 may be configured to obtain data/signals relating to the (portion of) subject. For example, the data acquisition device 110 may obtain image data of the subject.

In some embodiments, the data acquisition device 110 may include a single modality device. For example, the data acquisition device 110 may include a CT scanner, a PET scanner, a SPECT scanner, an MR scanner, an ultrasonic scanner, an ECT scanner, or the like, or a combination thereof. In some embodiment, the data acquisition device 110 may be a multi-modality device. For example, the data acquisition device 110 may include a PET-CT scanner, a PET-MR scanner, or the like, or a combination thereof. The following descriptions are provided, unless otherwise stated expressly, with reference to a CT scanner for illustration purposes and not intended to be limiting.

As illustrated, the CT scanner may include a gantry 111, a detector 112, a detecting region 113, a table 114, and a radiation source 115. The gantry 111 may support the detector 112 and the radiation source 115. The subject may be placed on the table 114 for scanning. The radiation source 115 may emit x-rays. The x-rays may be emitted from a focal spot using a high-intensity magnetic field to form an x-ray beam. The x-ray beam may travel toward the subject. The detector 112 may detect x-ray photons from the detecting region 113. In some embodiments, the detector 112 may include one or more detector units. The detector unit(s) may be and/or include single-row detector elements and/or multi-row detector elements.

The processing device 120 may process data and/or information. The data and/or information may be obtained from the data acquisition device 110 or retrieved from the storage device 130, the terminal device 140, and/or an external device (external to the hemodynamic parameters determination system 100) via the network 150. For example, the processing device 120 may generate a first vascular model and a second vascular model based on image data of a subject. The first vascular model and the second vascular model may correspond to at least one first blood vessel and at least one second blood vessel, respectively. As another example, the processing device 120 may couple the first vascular model with the second vascular model using an intermediate model to form a coupled vascular model. As still another example, the processing device 120 may determine at least one of a value of a first hemodynamic parameter of the at least one first blood vessel or a value of a second hemodynamic parameter of the at least one second blood vessel based on a flow field distribution of the coupled vascular model. In some embodiments, the processing device 120 may be a single server or a server group. The server group may be centralized or distributed. In some embodiments, the processing device 120 may be local or remote. For example, the processing device 120 may access information and/or data stored in the data acquisition device 110, the terminal device 140, and/or the storage device 130 via the network 150. As another example, the processing device 120 may be directly connected to the data acquisition device 110, the terminal device 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as illustrated in FIG. 2.

The storage device 130 may store data, instructions, and/or any other information. In some embodiments, the storage device 130 may store data obtained from the data acquisition device 110, the terminal device 140, and/or the processing device 120. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components (e.g., the processing device 120, the terminal device 140) of the hemodynamic parameters determination system 100. One or more components of the hemodynamic parameters determination system 100 may access the data or instructions stored in the storage device 130 via the network 150. In some embodiments, the storage device 130 may be directly connected to or communicate with one or more other components (e.g., the processing device 120, the terminal device 140) of the hemodynamic parameters determination system 100. In some embodiments, the storage device 130 may be part of the processing device 120.

The terminal device 140 may input/output signals, data, information, etc. In some embodiments, the terminal device 140 may enable a user interaction with the processing device 120. For example, the terminal device 140 may display an image of the subject on a screen 160. As another example, the terminal device 140 may obtain a user's input information through an input device (e.g., a keyboard, a touch screen, a brain wave monitoring device), and transmit the input information to the processing device 120 for further processing. The terminal device 140 may be a mobile device, a tablet computer, a laptop computer, a desktop computer, or the like, or any combination thereof. In some embodiments, the mobile device may include a home device, a wearable device, a virtual reality device, an augmented reality device, or the like, or any combination thereof. The home device may include a lighting device, a control device of an intelligent electrical apparatus, a monitoring device, a television, a video camera, an interphone, or the like, or any combination thereof. The wearable device may include a bracelet, a footgear, eyeglasses, a helmet, a watch, clothing, a backpack, an accessory, or the like, or any combination thereof. The virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing device 120 or a peripheral device of the processing device 120 (e.g., a console connected to and/or communicating with the processing device 120).

The network 150 may include any suitable network that can facilitate the exchange of information and/or data for the hemodynamic parameters determination system 100. In some embodiments, one or more components (e.g., the data acquisition device 110, the terminal device 140, the processing device 120, the storage device 130) of the hemodynamic parameters determination system 100 may communicate information and/or data with one or more other components of the hemodynamic parameters determination system 100 via the network 150. The network 150 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network, 4G network, 5G network), a frame relay network, a virtual private network (VPN), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the hemodynamic parameters determination system 100 may be connected to the network 150 to exchange data and/or information.

For illustration purposes, a coordinate system 170 is provided in FIG. 1. The coordinate system 170 may be a Cartesian system including an X-axis, a Y-axis, and a Z-axis. The X-axis and the Y-axis shown in FIG. 1 may be horizontal and the Z-axis may be vertical. As illustrated, the positive X direction along the X-axis may be from the left side to the right side of the table 114 viewed from the direction facing the front of the data acquisition device 110; the positive Y direction along the Y-axis shown in FIG. 1 may be from the end to the head of the table 114; the positive Z direction along the Z-axis shown in FIG. 1 may be from the lower part to the upper part of the data acquisition device 110.

It should be noted that the above description regarding the hemodynamic parameters determination system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the hemodynamic parameters determination system 100 may include one or more additional components and/or one or more components of the hemodynamic parameters determination system 100 described above may be omitted. In some embodiments, a component of the hemodynamic parameters determination system 100 may be implemented on two or more subcomponents. Two or more components of the hemodynamic parameters determination system 100 may be integrated into a single component.

FIG. 2 is a schematic diagram illustrating exemplary hardware and/or software components of an exemplary computing device according to some embodiments of the present disclosure. The computing device 200 may be configured to implement any component of the hemodynamic parameters determination system 100. For example, the data acquisition device 110, the processing device 120, the storage device 130, and/or the terminal device 140 may be implemented on the computing device 200. Although only one such computing device is shown for convenience, the computer functions relating to the hemodynamic parameters determination system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device 140 and/or the storage device 130. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the data acquisition device 110, the terminal device 140, the storage device 130, or any other component of the hemodynamic parameters determination system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the data acquisition device 110, the terminal device 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
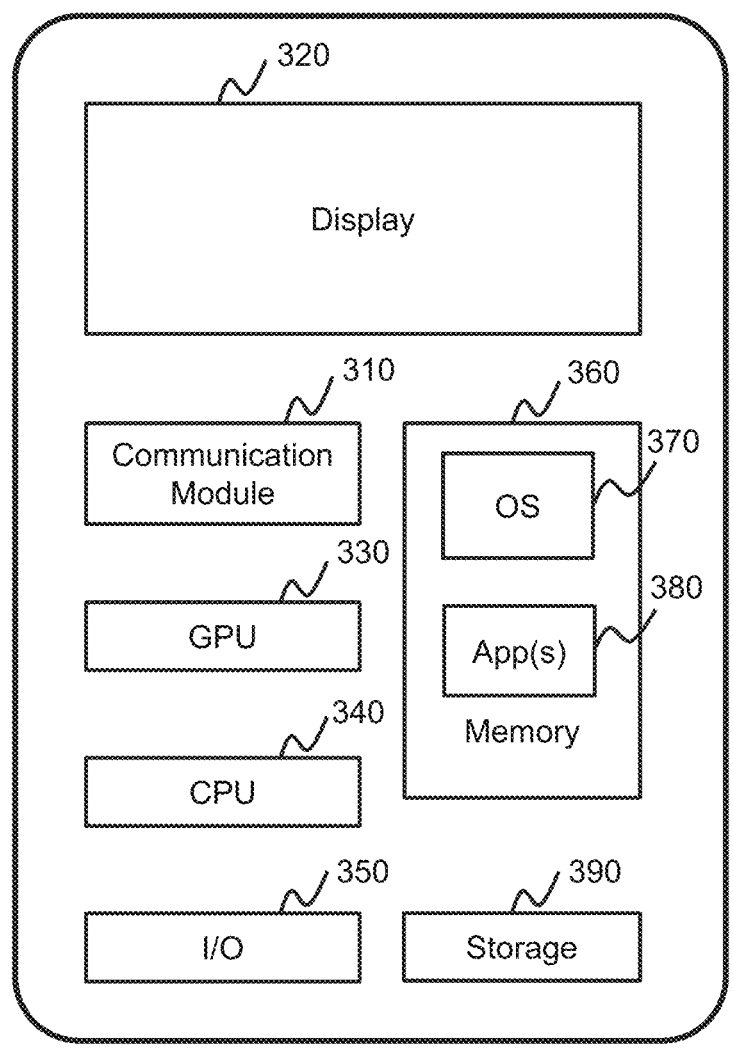
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the processing device 120 or the terminal device 140 may be implemented on the mobile device 300. As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the processor 210. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to imaging from the blood vessel parameter determination system on the mobile device 300. User interactions with the information stream may be achieved via the I/O devices 350 and provided to the processing device 120 and/or other components of the hemodynamic parameters determination system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
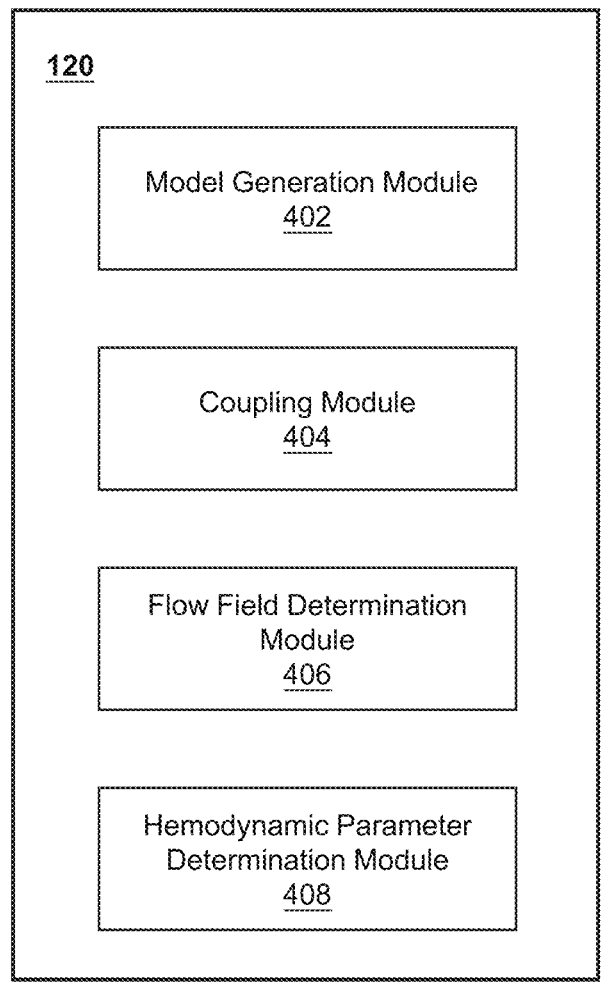
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 120 may include a model generation module 402, a coupling module 404, a flow field determination module 406, and a hemodynamic parameter determination module 408.

The model generation module 402 may generate one or more vascular models. In some embodiments, the model generation module 402 may generate a first vascular model and a second vascular model. The first vascular model and the second vascular model may correspond to at least one first blood vessel (or a portion thereof) and at least one second blood vessel (or a portion thereof) of a vascular system of a subject, respectively. In some embodiments, the first vascular model and/or the second vascular model based on image data of a subject. In some embodiments, the model generation module 402 may segment the at least one first blood vessel and at least one second blood vessel from the image data (e.g., images) of the subject. The model generation module 402 may extract features of the segmented at least one first blood vessel and/or at least one second blood vessel. The model generation module 402 may generate the first vascular model and the second vascular model based on the extracted features of the segmented at least one first blood vessel and at least one second blood vessel.

The coupling module 404 may couple the first vascular model with the second vascular model using an intermediate model to form a coupled vascular model. The intermediate model may include at least one connection model. The connection model may connect at least one first bifurcation end of the first vascular model and at least one second bifurcation end of the first vascular model. In some embodiments, the at least one connection model may include at least one flow resistance model. In some embodiments, a connection model may be a zero-dimensional model (i.e., a lumped parameter model), a one-dimensional model, a two-dimensional model, or a three-dimensional model, etc.

In some embodiments, the at least one connection model may be determined by a connection model reconstruction model. Merely by way of example, the first vascular model, the second vascular model, and image data of the subject may be inputted into the connection model reconstruction model, and the connection model reconstruction model may output the at least one connection model or data/information related to the at least one connection model. In some embodiments, the connection model reconstruction model may include a deep learning model, such as a Deep Neural Network (DNN) model, a Convolutional Neural Network (CNN) model, a Recurrent Neural Network (RNN) model, a Feature Pyramid Network (FPN) model, etc. Exemplary CNN models may include a V-Net model, a U-Net model, a Link-Net model, or the like, or any combination thereof.

The flow field determination module 406 may determine a flow field distribution of the coupled vascular model. In some embodiments, the flow field determination module 406 may set at least one of a first boundary condition of the first vascular model or a second boundary condition of the second vascular model. A boundary condition may refer to a blood flow condition of a boundary of a vascular model (e.g., the first vascular model or the second vascular model). A boundary may refer to an edge of a vascular model. For example, the boundary may be an exit, an entrance, a vascular wall, or the like, of a blood vessel.

In some embodiments, the boundary condition may include a pressure, a flow velocity, a flow resistance, a blood mass flow rate, etc., of the boundary. For example, the first boundary condition may include a first entrance flow velocity, a first entrance blood mass flow rate, a first entrance reference pressure, etc., at an entrance of the at least one first blood vessel, and/or a first exit flow velocity, a first exit blood mass flow rate, a first exit reference pressure, etc., at an exit of the at least one first blood vessel. The second boundary condition may include a second entrance flow velocity, a second entrance blood mass flow rate, a second entrance reference pressure, etc., at an entrance of the at least one second blood vessel, and/or a second exit flow velocity, a second exit blood mass flow rate, a second exit reference pressure, etc., at an exit of the at least one second blood vessel.

The hemodynamic parameter determination module 408 may determine at least one of a value of a first hemodynamic parameter of the at least one first blood vessel or a value of a second hemodynamic parameter of the at least one second blood vessel based on the flow field distribution of the coupled vascular model. A hemodynamic parameter of a blood vessel may represent the blood flow condition of the blood vessel. Exemplary hemodynamic parameters of a blood vessel may include a pressure, a wall stress, a WSS, a flow velocity, etc., at each of one or more positions of the blood vessel. For example, the first hemodynamic parameter may include a pressure, a wall stress, a WSS, a flow velocity, or the like, or any combination thereof, at each of one or more positions of the at least a part of the at least one first blood vessel. The second hemodynamic parameter may include a pressure, a wall stress, a WSS, a flow velocity, or the like, or any combination thereof, at each of one or more positions of the at least a part of the at least one second blood vessel. In some embodiments, the hemodynamic parameter of a blood vessel may include a mean value, a maximum value, a minimum value, a ratio, a difference, etc., of pressures, wall stresses, WSSes, and/or flow velocities at multiple positions of the blood vessel.

Figure 5:
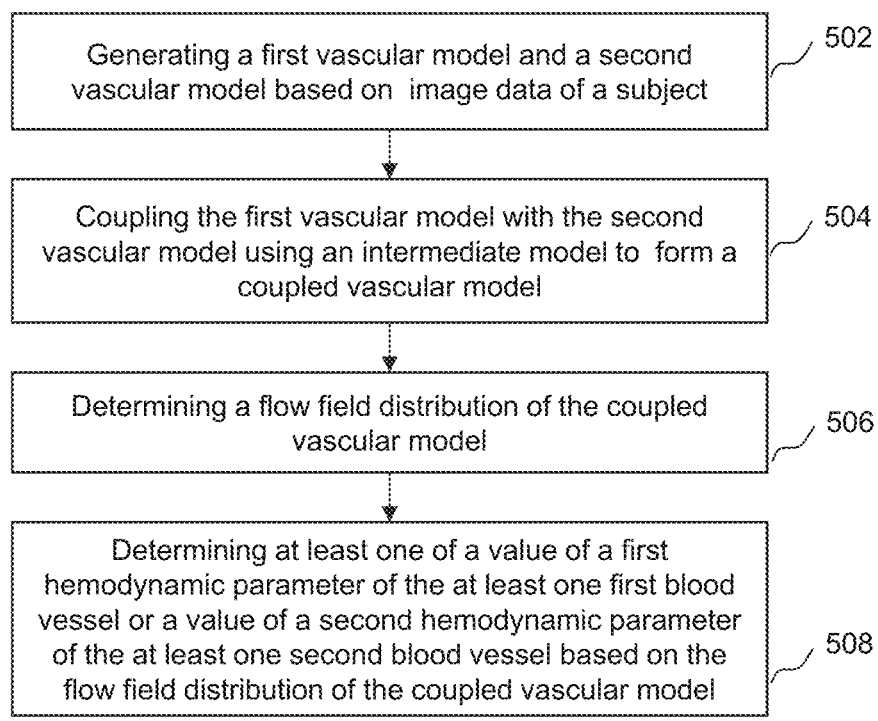
FIG. 5 is a flowchart illustrating an exemplary process for determining hemodynamic parameters of a subject according to some embodiments of the present disclosure.

FIG. 5 is a flowchart illustrating an exemplary process for determining hemodynamic parameters of a subject according to some embodiments of the present disclosure. In some embodiments, the process 500 may be executed by the hemodynamic parameters determination system 100. For example, the process 500 may be implemented as a set of instructions (e.g., an application) stored in a storage device (e.g., the storage device 130). The modules described in FIG. 4 and/or the processor 210 may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 502, the processing device 120 (e.g., the model generation module 402 or the processor 210) may generate a first vascular model and a second vascular model based on image data of a subject.

As used herein, the subject may include a biological subject and/or a non-biological subject that includes a vascular system. The vascular system may include at least one first blood vessel and at least one second blood vessel (or a portion thereof). For example, the subject may be a human being, an animal, or a portion thereof. The at least one first blood vessel or at least one second blood vessel may include a coronary artery blood vessel, an abdominal artery blood vessel, a brain artery blood vessel, a lower extremity artery blood vessel, etc. For example, the at least one first blood vessel or at least one second blood vessel may be an entire coronary artery, a left coronary artery, a right coronary artery, or a coronary branch (e.g., a left anterior descending (LAD), a left circumflex (LCX), a diagonal branch, etc.). The at least one first blood vessel and at least one second blood vessel may constitute a blood flow path of the vascular system of the subject.

In some embodiments, the image data of the subject may include a two-dimensional (2D) image (e.g., a slice image), a three-dimensional 3D image, a four-dimensional 4D image (e.g., a series of 3D images over time), and/or related image data, or the like, or any combination thereof. The image data of the subject may include one or more grayscale images and/or one or more color images. In some embodiments, the image data of the subject may include a medical image generated by a biomedical imaging technique as described elsewhere in this disclosure. For example, the image data of the subject may include a magmatic resonate angiograph (MRA) image, a computed tomography angiography (CTA) image, a digital subtraction angiography (DSA) image, etc. In some embodiments, the image data of the subject may include a coronary artery blood vessel image, a cervical vascular image, an aortic dissection image, an abdominal artery blood vessel image, a brain artery blood vessel image, a lower extremity artery blood vessel image, etc.

In some embodiments, the image data of the subject may correspond to at least two time phases of the subject; that is, the image data of the subject may include image data of at least two time phases. The image data of the at least two time phases may be obtained after a contrast agent flows through the at least one first blood vessel and the at least one second blood vessel of the subject. In some embodiments, the image data of the at least two time phases may include the image data of the subject at multiple different time points in a same physiological cycle (e.g., a sphygmic cycle) or different physiological cycles. Merely for illustration purposes, as for the liver of a subject, the at least two time phases may include an arterial phase, a portal phase, and a delayed phase. The processing device 120 may obtain image data corresponding to the arterial phase, the portal phase, and/or the delayed phase.

In some embodiments, the image data of the subject may be generated based on scanning data acquired using the data acquisition device 110 of the system 100 or an external data acquisition device. For example, the data acquisition device 110, such as a CT scanner, an MRI scanner, an X-ray scanner, a PET scanner, an ultrasound scanner, a digital imaging scanner, or the like, may be directed to scan the subject or a portion thereof (e.g., the chest of the subject). The processing device 120 may generate the image data of the subject based on the scanning data acquired by the data acquisition device 110. In some embodiments, the image data of the subject may be generated previously and stored in a storage device (e.g., the storage device 130, the storage 220, the storage 390, or an external source). The processing device 120 may retrieve the image data of the subject from the storage device. In some embodiments, the obtained image data of the subject may be preprocessed. The preprocessing may include image enhancement, image denoising, image smoothing, etc.

In some embodiments, the processing device 120 may segment the at least one first blood vessel and at least one second blood vessel from the image data (e.g., images) of the subject. In some embodiments, segmentation parameters set for segmenting the at least one first blood vessel from the image data may be the same as segmentation parameters set for segmenting at least one second blood vessel from the image data. Merely by way of example, the at least one first blood vessel and/or at least one second blood vessel may be segmented from the image data manually by a user (e.g., a doctor, an imaging specialist, a technician). Alternatively, the at least one first blood vessel and at least one second blood vessel may be segmented by the processing device 120 according to an image analysis algorithm (e.g., an image segmentation algorithm). Exemplary image segmentation algorithms may include an edge detection algorithm, a segmentation algorithm based on regions (e.g., a region growing segmentation algorithm, a thresholding segmentation algorithm, a clustering segmentation algorithm, etc.), a segmentation algorithm based on mathematical morphology, a segmentation algorithm based on statistics, a segmentation algorithm based on machine learning, a segmentation algorithm based on level sets, a segmentation algorithm based on trace, a segmentation algorithm based on fuzzy sets, or the like, or any combination thereof.

In some embodiments, the at least one first blood vessel may include a first main blood vessel and at least one first branch blood vessel. Similar to a structure of a tree, the first main blood vessel of the at least one first blood vessel may be similar to a trunk of the tree, and the at least one branch blood vessel of the at least one first blood vessel may be similar to at least one branch bifurcated from the trunk of the tree. Similarly, the at least one second blood vessel may include a second main blood vessel and at least one second branch blood vessel. In some embodiments, the way to segment the first/second main blood vessel and the way to segment the at least one first/second branch blood vessel may be the same or different. For example, a main blood vessel may be segmented by the processing device 120 automatically based on the image segmentation algorithm as described above. As another example, a branch blood vessel may be segmented by the processing device 120 semi-automatically based on the image segmentation algorithm and information provided by a user. The information provided by the user may include a parameter relating to the image segmentation algorithm, a position parameter relating to a region to be segmented, an adjustment, or rejection or confirmation of a preliminary segmentation result generated by the processing device 120, etc.

In some embodiments, the processing device 120 may extract features of the segmented at least one first blood vessel and/or at least one second blood vessel. The features of the segmented at least one first blood vessel and at least one second blood vessel may include one or more of a type (e.g., main blood vessel or branch blood vessel), a diameter, a centerline, a length, a curvature, etc., of the at least one first blood vessel and/or the at least one second blood vessel.

In some embodiments, the processing device 120 may generate the first vascular model and the second vascular model based on the extracted features of the segmented at least one first blood vessel and at least one second blood vessel. The first vascular model and the second vascular model may correspond to the at least one first blood vessel and the at least one second blood vessel, respectively. In some embodiments, the processing device 120 may generate the first vascular model and the second vascular model using a reconstruction technique. The reconstruction technique may include lofting or stretching blood vessels based on diameters or centerlines of the blood vessels to generate a vascular model. For example, the processing device 120 may determine a centerline of a blood vessel. The processing device 120 may further determine the contour of the blood vessel based on the centerline of the blood vessel. The reconstructed vascular model may correspond to a vascular shape or a blood flow shape of the blood vessel.

Merely by way of example, the at least one first blood vessel may include a portal vein, and the at least one second blood vessel may include a hepatic vein. Image data of a portal vein (also referred to as portal vein image data) may be generated by segmenting the portal vein from the image data of the subject automatically. Image data of a hepatic vein (also referred to as hepatic vein image data) may be generated by segmenting the hepatic vein from the image data of the subject automatically. The processing device 120 may generate a portal vein model based on the portal vein image data. The processing device 120 may generate a hepatic vein model based on the hepatic vein image data.

In 504, the processing device 120 (e.g., the coupling module 404 or the processor 210) may couple the first vascular model with the second vascular model using an intermediate model to form a coupled vascular model.

In some embodiments, the at least one first blood vessel may include a first main blood vessel and at least one first branch blood vessel. The at least one second blood vessel may include a second main blood vessel and at least one second branch blood vessel. In some embodiments, blood in the vascular system may flow into the at least one first blood vessel from the first main blood vessel, flow through the at least one first branch end blood vessel and the at least one second branch end blood vessel, and flow out from the second main blood vessel. For instance, an entrance of the first vascular model may correspond to an end of the first main blood vessel, and at least one exit of the first vascular model may correspond to an end of the at least one first branch end blood vessel. Correspondingly, at least one entrance of the second vascular model may correspond to an end of at least one second branch end blood vessel, and an exit of the second vascular model may correspond to an end of the at the second main blood vessel. Alternatively, blood in the vascular system may flow into the at least one second blood vessel from the second main blood vessel, flow through the at least one second branch end blood vessel and the at least one first branch end blood vessel, and flow out from the first main blood vessel. For instance, an entrance of the second vascular model may correspond to an end of the second main blood vessel, and at least one exit of the second vascular model may correspond to an end of the at least one second branch end blood vessel.
Correspondingly, at least one entrance of the first vascular model may correspond to an end of at least one first branch end blood vessel, and an exit of the first vascular model may correspond to an end of the at the first main blood vessel.

In some embodiments, the first vascular model may include at least one first bifurcation (i.e., branch). The at least one first bifurcation may include at least one first bifurcation end. A first bifurcation end of a first bifurcation may refer to a farthest segment of the first bifurcation. The first bifurcation may include a series of sequentially connected bifurcation segments of different levels (e.g., a first-level bifurcation segment, a second-level bifurcation segment, a third-level bifurcation segment, etc.). For example, for a first bifurcation of the first vascular model including a first-level bifurcation segment and a second-level bifurcation segment, the first bifurcation end of the first bifurcation may be the second-level bifurcation segment. Similarly, the second vascular model may include at least one second bifurcation. The at least one second bifurcation may include at least one second bifurcation end. A second bifurcation end of a second bifurcation may refer to a farthest segment of the second bifurcation.

In some embodiments, the at least one first bifurcation end may correspond to at least one first branch end blood vessel, respectively. A first branch end blood vessel may refer to a far most segment of a first branch blood vessel from the first main blood vessel of the at least one first vessel. The at least one second bifurcation end may correspond to at least one second branch end blood vessel, respectively. A second branch end blood vessel may refer to a far most segment of a second branch blood vessel from the second main blood vessel of the at least one second vessel.

In some embodiments, the processing device 120 may determine a correspondence relationship between the at least one first bifurcation end and the at least one second bifurcation end. According to the correspondence relationship, a first branch end blood vessel corresponding to a first bifurcation end and a corresponding second branch end blood vessel corresponding to a second bifurcation end may constitute a branch of a blood flow path, which may be formed by the at least one first blood vessel and the at least one second blood vessel.

Merely by way of example, the processing device 120 may determine information related to the at least one first bifurcation end and the at least one second bifurcation end based on the first vascular model, the second vascular model, the image data of the subject, or one or more specific physiological parameters of the subject. The one or more specific physiological parameters of the subject may include a fibrosis index, stiffness, a perfusion index, a diameter, a flow velocity, etc., of the at least one first blood vessel and/or the at least one second blood vessel. In some embodiments, at least one of the one or more specific physiological parameters of the subject may be obtained from the data acquisition device 110. For example, if the subject includes a liver, the one or more specific physiological parameters corresponding to the liver may include a liver fibrosis index, liver stiffness, a hepatic perfusion index, a diameter of a portal vein, a diameter of a hepatic artery, a diameter of a hepatic vein, a flow velocity of portal blood, a flow velocity of hepatic artery, and a flow velocity of hepatic vein, etc.

In some embodiments, the information related to the at least one first bifurcation end and the at least one second bifurcation end may include diameters, angles between the blood flow directions, directions, etc., of the at least one first bifurcation end and the at least one second bifurcation end, distances between the at least one first bifurcation end and the at least one second bifurcation end, a connection continuity between at least one first bifurcation end and the at least one second bifurcation end, etc.

The processing device 120 may determine the correspondence relationship between the at least one first bifurcation end and the at least one second bifurcation end based on the information related to at least one first bifurcation end and the at least one second bifurcation end. For example, if at least one preset condition is deemed satisfied based on the information related to a first bifurcation end and a second bifurcation end, the processing device 120 may determine that the first bifurcation end corresponds to the second bifurcation end. The at least one preset condition may include that a distance between the first bifurcation end and the second bifurcation end is below a first threshold, that a connection continuity between the first bifurcation end and the second bifurcation end is acceptable, that a difference between a diameter of the first bifurcation end and a diameter of the second bifurcation end is below a second threshold, that an angle between the blood flow directions of the first bifurcation end and the second bifurcation end is below a third threshold, that a difference between directions of the first bifurcation end and the second bifurcation end is below a fourth threshold, etc. The first threshold, the second threshold, the third threshold, and the fourth threshold may be set by a user, according to an empirical value, according to a default setting of the system 100, determined by the processing device 120 according to actual needs, etc.

In some embodiments, the processing device 120 may determine one or more bifurcation end pairs based on the correspondence relationship. According to the correspondence relationship, each of the one or more bifurcation end pairs may include a first bifurcation end and a corresponding second bifurcation end. In some embodiments, each of the at least one first bifurcation end may correspond to one of the at least one second bifurcation end. For instance, each of the at least one first bifurcation end and a corresponding second bifurcation end may constitute a bifurcation end pair. In some embodiments, a first bifurcation end may correspond to more than one second bifurcation ends. For instance, the first bifurcation end and each of the more than one second bifurcation ends may constitute a bifurcation end pair. In some embodiments, a second bifurcation end may correspond to more than one first bifurcation ends. For instance, the second bifurcation end and each of the corresponding more than one first bifurcation ends may constitute a bifurcation end pair. In this way, the processing device 120 may determine the one or more bifurcation end pairs based on the correspondence relationship.

In some embodiments, the intermediate model may include at least one connection model. Each of the at least one connection model may connect a bifurcation end pair. The processing device 120 may connect the at least one first bifurcation end, the at least one connection model, and the at least one second bifurcation end according to a certain correspondence relationship between the one or more bifurcation end pairs and the at least one connection model, thus generating the coupled vascular model. In some embodiments, the connection model may include at least one flow resistance model. In some embodiments, a connection model may be a zero-dimensional model (i.e., a centralized parameter model), a one-dimensional model, a two-dimensional model, or a three-dimensional model, etc.

Figure 7:
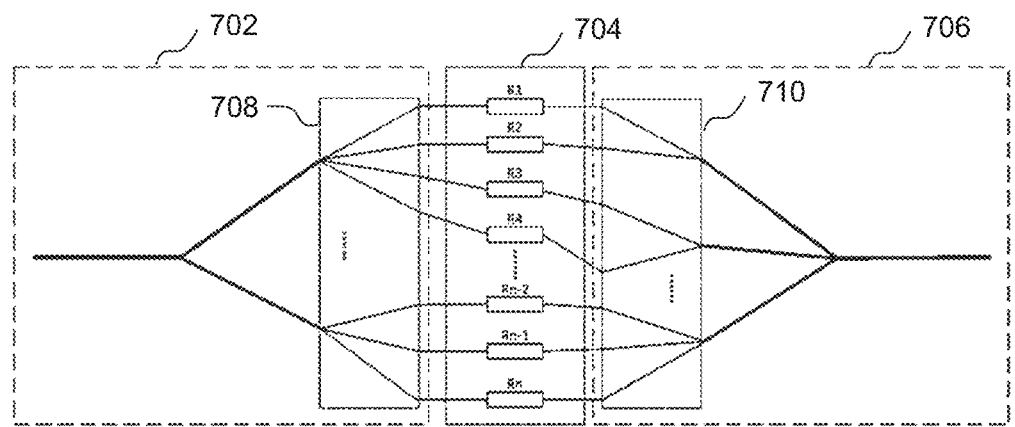
FIG. 7 is a schematic diagram illustrating an exemplary coupled vascular model according to some embodiments of the present disclosure.

In some embodiments, the at least one connection model may correspond at least one intermediate blood vessel that connects the at least one first branch end blood vessel and the at least one second branch end blood vessel. A flow resistance of each of the at least one intermediate blood vessel may be determined based on the at least one connection model. For example, FIG. 7 is a schematic diagram 700 illustrating an exemplary coupled vascular model according to some embodiments of the present disclosure. As shown in FIG. 7, a first vascular model 702, an intermediate model 704, and a second vascular model 706 may form the coupled vascular model. The first vascular model 702 may include multiple first bifurcation ends, e.g., first bifurcation ends 708. The second vascular model 706 may include multiple second bifurcation ends, e.g., second bifurcation ends 710. The intermediate model 704 may include multiple connection models. The multiple connection models may be flow resistance models $R_1$, $R_2$, . . . , and $R_n$. The flow resistance models $R_1$, $R_2$, . . . , and $R_n$ may be zero-dimensional flow resistance models. Each of the multiple first bifurcation ends 708 and a corresponding second bifurcation end 710 may be connected through a corresponding zero-dimensional flow resistance model. A count of the multiple first bifurcation ends 708, a count of the multiple second bifurcation ends 710, and a count of the multiple zero-dimensional flow resistance models may be the same (i.e., n, an integer larger than or equal to 1).

In some embodiments, the at least one connection model may be determined based on the first vascular model, the second vascular model, the image data of the subject, the correspondence relationship between the at least one first bifurcation end of the first vascular model and the at least one second bifurcation end of the second vascular model, image data, and one or more specific physiological parameters of the subject. For example, if each of the at least one connection model is a zero-dimensional flow resistance model (i.e., a centralized parameter model), the processing device 120 may determine at least one intermediate blood vessel that connects at least one first branch end blood vessel and at least one second branch end blood vessel. Each of the at least one intermediate blood vessel may correspond a connection model. The processing device 120 may determine a flow resistance of each of at least one intermediate blood vessel based on image data, and the one or more specific physiological parameters of the subject. The processing device 120 may further designate the flow resistance of each intermediate blood vessel as a flow resistance of a connection model corresponding the intermediate blood vessel to generate the corresponding connection model.

In some embodiments, the at least one connection model may be determined by a connection model reconstruction model. Merely by way of example, the first vascular model, the second vascular model, the correspondence relationship between the at least one first bifurcation end of the first vascular model and the at least one second bifurcation end of the second vascular model, image data, and clinical information of the subject may be inputted into the connection model reconstruction model, and the connection model reconstruction model may output the at least one connection model or data/information related to the at least one connection model. In some embodiments, the connection model reconstruction model may include a deep learning model, such as a Deep Neural Network (DNN) model, a Convolutional Neural Network (CNN) model, a Recurrent Neural Network (RNN) model, a Feature Pyramid Network (FPN) model, etc. Exemplary CNN models may include a V-Net model, a U-Net model, a Link-Net model, or the like, or any combination thereof.

Merely by way of example, the connection model reconstruction model may be trained according to a supervised learning algorithm or an unsupervised learning algorithm by the processing device 120 or another computing device (e.g., a computing device of a vendor of a connection model). The processing device 120 may obtain one or more training samples and a preliminary model. Each training sample may include a sample first vascular model, the sample second vascular model, the correspondence relationship between the at least one first bifurcation end of the sample first vascular model and the at least one second bifurcation end of the sample second vascular model, sample image data, and clinical information, of a sample subject, and at least one reference parameter. The at least one reference parameter may include a diameter, a centerline, a length, a curvature, a pressure, a flow velocity, etc., related to the sample first vascular model, the sample second vascular model, and/or the sample image data. The preliminary model to be trained may include one or more model parameters, such as a count (or number) of layers, a count (or number) of nodes, a loss function, or the like, or any combination thereof. Before training, the preliminary model may have one or more initial parameter values of the model parameter(s).

The training of the preliminary model may include one or more iterations to iteratively update the model parameters of the preliminary model based on the training sample(s) until a termination condition is satisfied in a certain iteration. Exemplary termination conditions may be that the value of a loss function obtained in the certain iteration is less than a threshold value, that a certain count of iterations has been performed, that the loss function converges such that the difference of the values of the loss function obtained in a previous iteration and the current iteration is within a threshold value, etc. The loss function may be used to measure a discrepancy between a result predicted by the preliminary model in an iteration and the at least one reference parameter. Exemplary loss functions may include a focal loss function, a log loss function, a cross-entropy loss, a Dice ratio, or the like. If the termination condition is not satisfied in a current iteration, the processing device 120 may further update the preliminary model to be used in a next iteration according to, for example, a backpropagation algorithm. If the termination condition is satisfied in the current iteration, the processing device 120 may designate the preliminary model in the current iteration as the at least one connection model.

In some embodiments, the processing device 120 may determine that at least one connection model based on a phantom manufactured to mimic actual conditions of the subject. For example, physiological activities of a liver including a portal vein and a hepatic vein may be modeled using a liver phantom manufactured according to actual conditions of the liver. The liver phantom may have a structure/material the same as or similar to the liver. Besides, the liver phantom may have an input fluid (e.g., blood) the same as or similar to the liver. At least one parameter (e.g., a flow resistance, a flow velocity, a flow volume, a pressure etc.) of a portion of the liver phantom corresponding to the at least one connection model may be measured or calculated. The processing device 120 may determine the at least one connection model based on the at least one parameter.

In 506, the processing device 120 (e.g., the flow field determination module 406 or the processor 210) may determine a flow field distribution of the coupled vascular model.

In some embodiments, the processing device 120 may set at least one of a first boundary condition of the first vascular model or a second boundary condition of the second vascular model. A boundary condition may refer to a blood flow condition of a boundary of a vascular model (e.g., the first vascular model or the second vascular model). A boundary refers to an edge of a vascular model. For example, the boundary may be an exit, an entrance, a vascular wall, or the like, of a blood vessel.

Figure 8:
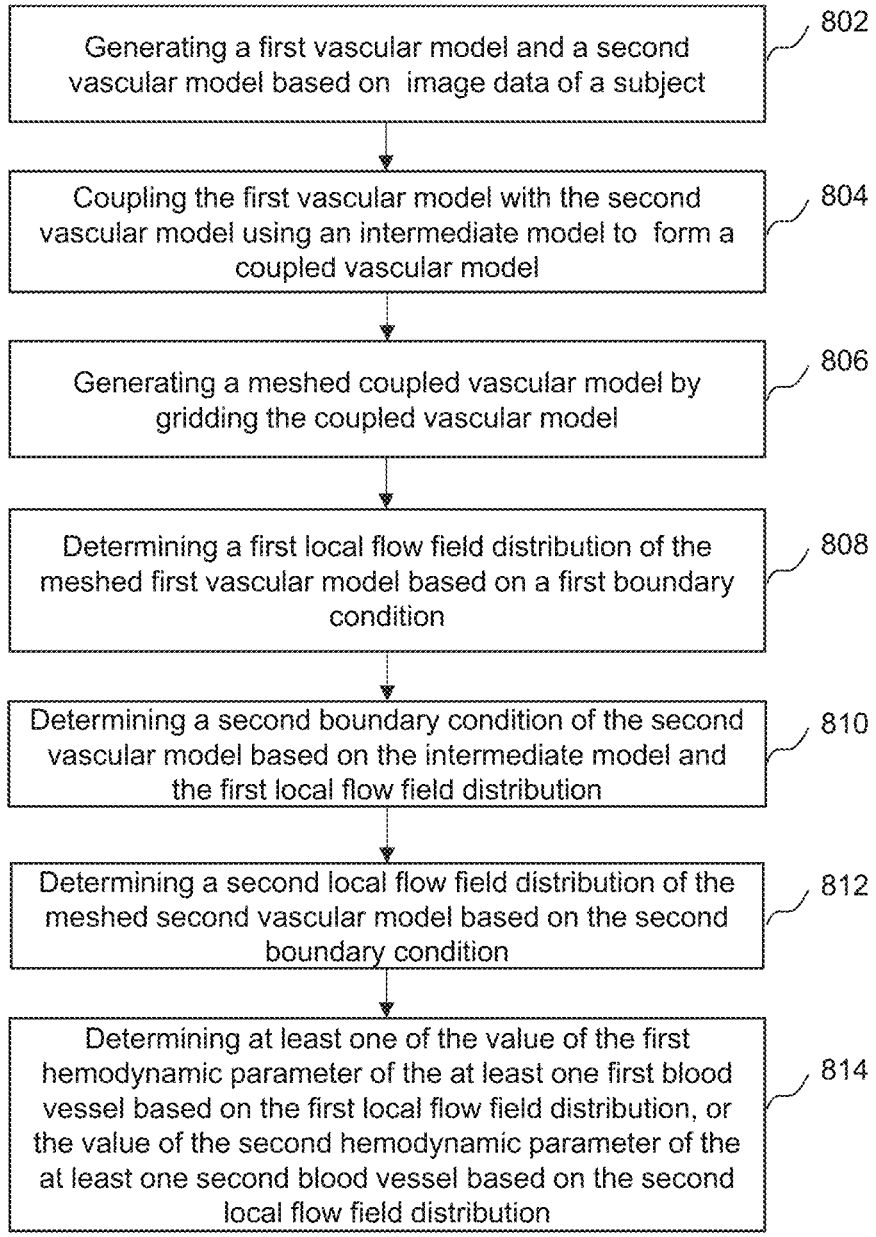
FIG. 8 is a schematic diagram illustrating an exemplary process for determining hemodynamic parameters of a subject according to some embodiments of the present disclosure.

In some embodiments, the boundary condition may include a pressure, a flow velocity, a flow resistance, a pressure intensity, a stress, etc., of the boundary For example, the first boundary condition may include a first entrance flow velocity, a first entrance blood mass flow rate, a first entrance reference pressure, etc., at an entrance of the at least one first blood vessel, and/or a first exit flow velocity, a first exit blood mass flow rate, a first exit reference pressure, etc., at an exit of the at least one first blood vessel. The second boundary condition may include a second entrance flow velocity, a second entrance blood mass flow rate, a second entrance reference pressure, etc., at an entrance of the at least one second blood vessel, and/or a second exit flow velocity, a second exit blood mass flow rate, a second exit reference pressure, etc., at an exit of the at least one second blood vessel. In some embodiments, the determination of the first boundary condition of the first vascular model and the second boundary condition of the second vascular model may be found in the description of 808 of the process 800 as illustrated in FIG. 8.

In some embodiments, the processing device 120 may determine a flow field distribution of the coupled vascular model based on the at least one of the first boundary condition of the first vascular model or the second boundary condition of the second vascular model. The flow field distribution of the coupled vascular model may include a pressure field distribution, a wall stress field distribution, a wall shear stress (WSS) field distribution, a flow velocity field distribution, or the like, or any combination thereof, of the coupled vascular model.

In some embodiments, the processing device 120 may determine a flow field distribution of the coupled vascular model based on the at least one of the first boundary condition of the first vascular model or the second boundary condition of the second vascular model according to an algorithm, for example, a computational fluid dynamics (CFD) algorithm.

For illustration purposes, the determination of a flow field distribution of a vascular model according to a CFD algorithm will be described hereinafter. CFD is an interdisciplinary method relating to mathematics, fluid mechanics, and computer science. The use of CFD may include simulating and analyzing fluid mechanics problems by solving control equations of fluid mechanics with computers and numerical methods. According to a predetermined vascular model (also referred to as a preliminary vascular model), boundary conditions, and/or parameters of the predetermined vascular model, a flow field distribution of a 3D vascular model (e.g., the first vascular model or the second vascular model) may be obtained. A control equation based on Euler equations, Navier-Stokes equations, and/or a Lattice Boltzmann method may be used in obtaining the flow field distribution. Alternatively, a discretization technique such as a finite difference technique, a finite volume technique, a finite element technique, a boundary element technique, a spectral technique, a Lattice Boltzmann technique, a meshless technique, or the like, or any combination thereof may be used in obtaining the flow field distribution. In some embodiments, a fluid of the flow field computation that used in obtaining the parameters may be viscous or non-viscous. In some embodiments, the fluid may be compressible or incompressible. The fluid may be a laminar flow or a turbulent flow. The fluid may be a steady flow or an unsteady flow. A corresponding control equation or simulation method may be selected based on physical features of the simulated fluid. For example, the Euler equations or the Lattice Boltzmann method may be selected for the flow field computation of the non-viscous fluid, while the Navier-Stokes equations or the Lattice Boltzmann method may be selected for the flow field computation of the viscous fluid. For example, a computation of the CFD for the vascular model may use the Navier-Stokes equations (1) and (2):

$$\frac{\partial \rho}{\partial t} + \nabla \cdot (\rho u) = 0, \tag{1}$$

and $$\frac{\partial \rho u}{\partial t} + \nabla \cdot (\rho u u) = \nabla \cdot \sigma. \tag{2}$$

where ρ may denote the blood density, u may denote the flow velocity, t may denote the time, and σ may denote the blood stress (which is determined by the pressure p and the blood viscosity).

The processing device 120 may determine, according to the exemplified equations or algorithms, a physical state and/or a flow field distribution of the coupled vascular model. For example, the processing device 120 may determine a flow field distribution, such as a pressure field distribution, a wall stress field distribution, a WSS field distribution, a flow velocity field distribution, or the like, or any combination thereof, of a coupled vascular model regarding a portal vein and a hepatic vein.

In some embodiments, the processing device 120 may further generate a meshed coupled vascular model by gridding the coupled vascular model. The processing device 120 may determine the flow field distribution of the coupled vascular model based on the meshed coupled vascular model, and the at least one of the first boundary condition or the second boundary condition according to an algorithm (e.g., a CFD algorithm). Detailed descriptions regarding the meshed coupled vascular model can be found elsewhere in the present disclosure. See, for example, FIG. 8 and relevant descriptions thereof.

In 508, the processing device 120 (e.g., the hemodynamic parameter determination module 408 or the processor 210) may determine at least one of a value of a first hemodynamic parameter of the at least one first blood vessel or a value of a second hemodynamic parameter of the at least one second blood vessel based on the flow field distribution of the coupled vascular model. A hemodynamic parameter of a blood vessel may represent the blood flow condition of the blood vessel. Exemplary hemodynamic parameters of a blood vessel may include a pressure, a wall stress, a WSS, a flow velocity, etc., at each of one or more positions of the blood vessel. For example, the first hemodynamic parameter may include a pressure, a wall stress, a WSS, a flow velocity, or the like, or any combination thereof, at each of one or more positions of the at least a part of the at least one first blood vessel. The second hemodynamic parameter may include a pressure, a wall stress, a WSS, a flow velocity, or the like, or any combination thereof, at each of one or more positions of the at least a part of the at least one second blood vessel.

In some embodiments, the processing device 120 may determine at least one of the value of the first hemodynamic parameter of the at least one first blood vessel based on a first local flow field distribution, or the value of the second hemodynamic parameter of the at least one second blood vessel based on a second local flow field distribution. The first local flow field distribution may refer to a flow field distribution of the first vascular model. The second local flow field distribution may refer to a flow field distribution of the second vascular model. The determination of the first local flow field distribution may be found in the description of 808 of the process 800 as illustrated FIG. 8. The determination of the second local flow field distribution may be found in the description of 812 of the process 800 as illustrated FIG. 8.

In some embodiments, the processing device 120 may determine a value of a hemodynamic parameter corresponding to any point or area in the coupled vascular model according to location information of the point or area. For example, the location information of the point may be represented by three-dimensional coordinate information of the point with reference to a coordinate system (e.g., a Cartesian coordinate system associated with the data acquisition device 110). The processing device 120 may determine the three-dimensional coordinate information of the point based on an input, a manual click, etc., of a user via an interface of a terminal device (e.g., the terminal device 140).

In some embodiments, the processing device 120 may determine a value (e.g., an average, a maximum, a minimum, etc.) of a hemodynamic parameter corresponding to a region (e.g., a section, a curve, a volume, etc.) in the coupled vascular model. For example, the region may be determined based on an input, a manual operation, etc., of a user via an interface of a terminal device (e.g., the terminal device 140).

In some embodiments, the processing device 120 may generate a curve or a table of a relationship between the value of the hemodynamic parameter corresponding to a point or a region in the coupled vascular model and a target parameter (e.g., time points of one or more time phases). According to the curve or table of the relationship, the value of the hemodynamic parameter corresponding to the point and/or the region at any time may be obtained.

In some embodiments, the at least one first blood vessel may include at least one artery blood vessel and the at least one second blood vessel may include at least one vein blood vessel. In some embodiments, the at least one first blood vessel may include at least one vein blood vessel and the at least one second blood vessel may also include at least one vein blood vessel. For example, the at least one first blood vessel may include a portal vein, and the at least one second blood vessel may include a hepatic vein. The at least one first blood vessel may include a first main blood vessel and at least one first branch blood vessel. The at least one second blood vessel may include a second main blood vessel and at least one second branch blood vessel. The processing device 120 may further determine a value of a pressure gradient between the first main blood vessel and the second main blood vessel according to a pressure of the first main blood vessel and the second main blood vessel. Merely by way of example, the at least one first blood vessel may include a portal vein, and the at least one second blood vessel may include a hepatic vein. The processing device 120 may determine values of pressures of the portal vein and the hepatic vein. The processing device 120 may further determine a value of a pressure gradient between the main portal vein and the main hepatic vein, which may be used for a diagnosis of portal hypertension.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional operation to transmit the determination result of value of the hemodynamic parameter to a terminal device for display.

Figure 6:
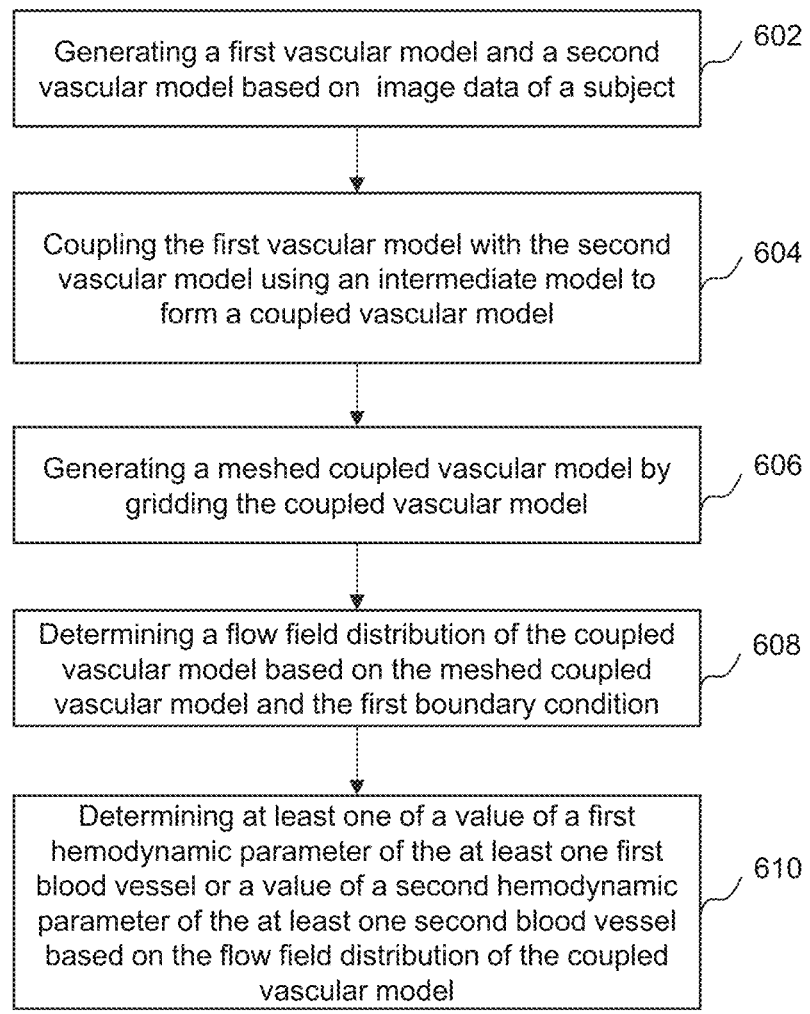
FIG. 6 is a flowchart illustrating an exemplary process for determining hemodynamic parameters of a subject according to some embodiments of the present disclosure.

FIG. 6 is a flowchart illustrating an exemplary process for determining hemodynamic parameters of a subject according to some embodiments of the present disclosure. In some embodiments, the process 600 may be executed by the hemodynamic parameters determination system 100. For example, the process 600 may be implemented as a set of instructions (e.g., an application) stored in a storage device (e.g., the storage device 130). The modules described in FIG. 4 and/or the processor 210 may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 602, the processing device 120 (e.g., the model generation module 402 or the processor 210) may generate a first vascular model and a second vascular model based on image data of a subject. In some embodiments, the processing device 120 may segment the at least one first blood vessel and at least one second blood vessel from the image data (e.g., images) of the subject. The processing device 120 may extract features of the segmented at least one first blood vessel and/or at least one second blood vessel. The processing device 120 may further generate the first vascular model and the second vascular model based on the extracted features of the segmented at least one first blood vessel and at least one second blood vessel. In some embodiments, the operation 602 may be similar to or the same as the operation 502 of the process 500 as illustrated in FIG. 5, the descriptions of which are not repeated here.

In 604, the processing device 120 (e.g., the coupling module 404 or the processor 210) may couple the first vascular model with the second vascular model using an intermediate model to form a coupled vascular model. The intermediate model may include at least one connection model. Each of the at least one connection model may connect a bifurcation end pair. The processing device 120 may connect at least one first bifurcation end, at least one connection model, and at least one second bifurcation end according to a certain correspondence relationship between one or more bifurcation end pairs and the at least one connection model, thus generating the coupled vascular model. In some embodiments, the operation 604 may be similar to or the same as the operation 504 of the process 500 as illustrated in FIG. 5, the descriptions of which are not repeated here.

In 606, the processing device 120 (e.g., the flow field determination module 406 or the processor 210) may generate a meshed coupled vascular model by gridding the coupled vascular model. Detailed descriptions regarding the meshed coupled vascular model can be found elsewhere in the present disclosure. See, for example, FIG. 8 and relevant descriptions thereof.

In 608, the processing device 120 (e.g., the flow field determination module 406 or the processor 210) may determine a flow field distribution of the coupled vascular model based on the meshed coupled vascular model and the first boundary condition. In some embodiments, the processing device 120 may set the first boundary condition of the first vascular model. In some embodiments, the determination of the first boundary condition of the first vascular model may be found in the description of 808 of the process 800 as illustrated in FIG. 8. In some embodiments, determination of the flow field distribution of the coupled vascular model based on the meshed coupled vascular model and the first boundary condition may be similar to or the same as the operation 506 of the process 500 as illustrated in FIG. 5, the descriptions of which are not repeated here.

In 610, the processing device 120 (e.g., the hemodynamic parameter determination module 408 or the processor 210) may determine at least one of a value of a first hemodynamic parameter of the at least one first blood vessel or a value of a second hemodynamic parameter of the at least one second blood vessel based on the flow field distribution of the coupled vascular model. A hemodynamic parameter of a blood vessel may represent the blood flow condition of the blood vessel. Exemplary hemodynamic parameters of a blood vessel may include a pressure, a wall stress, a WSS, a flow velocity, etc., at each of one or more positions of the blood vessel. In some embodiments, the processing device 120 may determine at least one of the value of the first hemodynamic parameter of the at least one first blood vessel based on a first local flow field distribution, or the value of the second hemodynamic parameter of the at least one second blood vessel based on a second local flow field distribution. The first local flow field distribution may refer to a flow field distribution of the first vascular model. The second local flow field distribution may refer to a flow field distribution of the second vascular model. The determination of the first local flow field distribution may be found in the description of 808 of the process 800 as illustrated FIG. 8. The determination of the second local flow field distribution may be found in the description of 812 of the process 800 as illustrated FIG. 8. In some embodiments, the operation 610 may be similar to or the same as the operation 508 of the process 500 as illustrated in FIG. 5.

According to the embodiments provided in the process 500 or 600, the processing device 120 may generate a first vascular model and a second vascular model based on image data of a subject, and form a coupled vascular model by coupling the first vascular model with the second vascular model using an intermediate model. The processing device 120 may further determine a flow field distribution of the coupled vascular model, and at least one of a value of a first hemodynamic parameter of the at least one first blood vessel or a value of a second hemodynamic parameter of the at least one second blood vessel based on the flow field distribution of the coupled vascular model. By performing the operations exemplified above, the value of the hemodynamic parameter of a blood vessel may be determined in a non-invasive, and the accuracy of the value of the hemodynamic parameter may be effectively improved.

FIG. 8 is a flowchart illustrating an exemplary process for determining hemodynamic parameters of a subject according to some embodiments of the present disclosure. In some embodiments, the process 800 may be executed by the hemodynamic parameters determination system 100. For example, the process 800 may be implemented as a set of instructions (e.g., an application) stored in a storage device (e.g., the storage device 130). The modules described in FIG. 4 and/or the processor 210 may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 802, the processing device 120 (e.g., the model generation module 402 or the processor 210) may generate a first vascular model and a second vascular model based on image data of a subject. In some embodiments, the processing device 120 may segment the at least one first blood vessel and at least one second blood vessel from the image data (e.g., images) of the subject. The processing device 120 may extract features of the segmented at least one first blood vessel and/or at least one second blood vessel. The processing device 120 may further generate the first vascular model and the second vascular model based on the extracted features of the segmented at least one first blood vessel and at least one second blood vessel. In some embodiments, the operation 802 may be similar to or the same as the operation 502 of the process 500 as illustrated in FIG. 5.

In 804, the processing device 120 (e.g., the coupling module 404 or the processor 210) may couple the first vascular model with the second vascular model using an intermediate model to form a coupled vascular model. The intermediate model may include at least one connection model. Each of the at least one connection model may connect a bifurcation end pair. The processing device 120 may connect at least one first bifurcation end, at least one connection model, and at least one second bifurcation end according to a certain correspondence relationship between one or more bifurcation end pairs and the at least one connection model, thus generating the coupled vascular model. In some embodiments, the operation 604 may be similar to or the same as the operation 504 of the process 500 as illustrated in FIG. 5, the descriptions of which are not repeated here.

In 806, the processing device 120 (e.g., the flow field determination module 406 or the processor 210) may generate a meshed coupled vascular model by gridding the coupled vascular model. The meshed coupled vascular model may include a meshed first vascular model and a meshed second vascular model.

In some embodiments, the meshed coupled vascular model may include a structured grid model or an unstructured grid model. The structured grid model refers to a grid model in which grids (e.g., hexahedron grids) are arranged in an orderly manner that is in conformity with a rule and positional relationships between adjacent grids are clear. The unstructured grid model refers to a grid model in which grids (e.g., tetrahedron grids) are not arranged in an orderly manner. In some embodiments, the meshed coupled vascular model may include a surface grid model or a volume grid model. The surface grid model refers to a grid model that only contains grids on surfaces of the grid model. The volume grid model refers to a grid model that contains grids on both surfaces and interior of the grid model.

In some embodiments, the processing device 120 may determine one or more grid division parameters based on feature information of the coupled vascular model. The one or more grid division parameters may include a grid density, a grid size, a grid count, a grid shape, etc. The feature information of the coupled vascular model may include at least one of a type, a diameter, a curvature, a structure, etc., of the coupled vascular model. For example, the processing device 120 may determine the grid density based on the curvature of the coupled vascular model. If it is determined that the curvature of the coupled vascular model is proportional to the grid density, the processing device 120 may set a larger grid density at a position with a larger curvature and a smaller grid density at a position with a small curvature. As another example, the processing device 120 may determine the grid size based on the diameter of the coupled vascular model or the structure of the coupled vascular model. Merely for illustration, the processing device 120 may set a larger grid size at a position with a larger diameter or a relatively simple structure and a smaller grid size at a position with a smaller diameter or a relatively complex structure.

In some embodiments, the processing device 120 may generate the meshed coupled vascular model by performing a grid division on the coupled vascular model based on the one or more grid division parameters. A grid division refers to an operation that may divide a region of interest (ROI) into a limited number (or count) of sub-regions or sub-elements. For example, the processing device 120 may perform a 2D surface grid division (also referred a 2D surface gridding) on a surface corresponding to a boundary region of a coupled vascular model to generate a surface grid model. The 2D surface grid division may be performed by dividing a surface corresponding to the boundary region of the coupled vascular model using 2D grids. Merely by way of example, surface grids of a side wall of the coupled vascular model may be generated. For example, the side wall may be divided according to a surface grid subdivision algorithm. The surface grid subdivision algorithm may include a mapping technique, an automated grid generation technique, etc. The mapping technique may include mapping the side wall to a surface, dividing the surface by a 2D grid division method, and mapping the divided grids to the side wall. The automated grid generation technique may include dividing the side wall into multiple approximate surfaces according to curvatures of different regions of the side wall, and then implementing the 2D grid division.

As another example, the processing device 120 may perform a volume grid division (also referred a 3D gridding) on the coupled vascular model to generate a volume grid model. The volume grid division may be performed by dividing the coupled vascular model using 3D grids. Merely by way of example, volume grids of the coupled vascular model may be generated based on the 2D surface grid divisions of boundary regions and side walls. The volume grid division may include dividing the coupled vascular model into 3D grids. The 3D grids may include a tetrahedral grid, a hexahedral mesh, a prismatic grid (e.g., a boundary layer grid), a mixture grid of tetrahedron and hexahedron, a Cartesian grid, a ball filling grid, etc.

In some embodiments, the processing device 120 may generate the meshed coupled vascular model by gridding the coupled vascular model using one or more grid division algorithms. Exemplary grid division algorithms may include a Loop algorithm, a butterfly subdivision algorithm, a Catmull-Clark algorithm, a Doo-Sabin algorithm, a Delaunay triangular division algorithm, etc.

In 808, the processing device 120 (e.g., the flow field determination module 406 or the processor 210) may determine a first local flow field distribution of the meshed first vascular model based on a first boundary condition. In some embodiments, the first local flow field distribution may include a first local pressure field distribution, a first local wall stress field distribution, a first local WSS field distribution, a first local flow velocity field distribution, or the like, or any combination thereof, of the meshed first vascular model.

In some embodiments, the first boundary condition may include at least one of a first entrance flow velocity, a first entrance blood mass flow rate, or a first entrance reference pressure at an entrance of the at least one first blood vessel, or a first exit flow velocity, a first exit blood mass flow rate, or a first exit reference pressure at an exit of the at least one first blood vessel.

In some embodiments, an entrance of the first vascular model corresponds to a start of the first main blood vessel, and at least one exit of the first vascular model corresponds to an end of the at least one first branch end blood vessel. In some embodiments, the first boundary condition may be determined based on specific physiological parameters of the subject and/or the first vascular model. The specific physiological parameters of the subject may include at least one flow velocity, at least one pressure, etc., of the at least one first blood vessel and at least one second blood vessel.

For instance, the first entrance flow velocity may be determined based on the specific physiological parameters of the subject. Merely for illustration, the first entrance flow velocity may be measured non-invasively using a detector (e.g., an ultrasonic detector). The first entrance blood mass flow rate may be determined based on the first entrance flow velocity. For example, the processing device 120 may determine a first entrance flow velocity based on the specific physiological parameters of the subject. The processing device 120 may determine the first entrance blood mass flow rate based on the determined first entrance flow velocity. In some embodiments, the first exit flow velocity may be determined in a way similar to the determination of the first entrance flow velocity. For example, the first exit flow velocity may be determined based on the specific physiological parameters of the subject. In some embodiments, the first exit flow velocity may be determined based on the first entrance flow velocity. For example, the first exit flow velocity may be determined based on a size (e.g., a diameter, an area, etc.) of the exit of the first blood vessel, and the first entrance flow velocity. The first exit blood mass flow rate may be determined based on the first exit flow velocity or the first entrance blood mass flow rate. For example, the processing device 120 may determine a firstexit blood mass flow rate based on a size (e.g., a diameter) of the exit of the first blood vessel, and the first entrance blood mass flow rate.

The first entrance reference pressure may refer to a reference pressure at the entrance of the at least one first blood vessel. The first exit reference pressure may refer to a reference pressure at the exit of the at least one first blood vessel. In some embodiments, the first entrance reference pressure and/or the first exit reference pressure may be determined based on specific physiological parameters of the subject. For example, a pressure measured by a blood-pressure meter may be set as the first entrance reference pressure and/or the first exit reference pressure. In some embodiments, the first entrance reference pressure and/or the first exit reference pressure may be set by a user, according to default settings of the hemodynamic parameters determination system 100, etc. In some embodiments, the processing device 120 may set the first entrance reference pressure or the first exit reference pressure to a specific value, such as 0 etc. In some embodiments, the processing device 120 may set the first entrance reference pressure or the first exit reference pressure to any suitable value (e.g., any positive value), which is not limiting.

In some embodiments, the processing device 120 may determine the first local flow field distribution of the meshed first vascular model based on the first boundary condition according to a specific algorithm, for example, the CFD algorithm.

In 810, the processing device 120 (e.g., the flow field determination module 406 or the processor 210) may determine a second boundary condition of the second vascular model based on the intermediate model and the first local flow field distribution.

In some embodiments, the second boundary condition may include at least one of a second entrance flow velocity, a second entrance blood mass flow rate, or a second entrance reference pressure at an entrance of the at least one second blood vessel, or a second exit flow velocity, a second exit blood mass flow rate, or a second exit reference pressure at an exit of the at least one second blood vessel.

In some embodiments, at least one entrance of the second vascular model corresponds to an end of at least one second branch end blood vessel, and an exit of the second vascular model corresponds to an end of the at the second main blood vessel. In some embodiments, the second boundary condition may be determined based on one or more of the specific physiological parameters of the subject, the second vascular model, the first local flow field distribution, etc. For instance, the second entrance flow velocity may be determined based on specific physiological parameters of the subject. Merely for illustration, the second entrance flow velocity may be measured non-invasively using a detector (e.g., an ultrasonic detector). The second entrance blood mass flow rate may be determined based on the second entrance flow velocity. As another example, the processing device 120 may determine the second entrance blood mass flow rate based on the first local flow field distribution. Merely for illustration, the second entrance blood mass flow rate of a second entrance may be equal to the first exit blood mass flow rate of a first exit corresponding to the second entrance. The processing device 120 may further determine the second entrance flow velocity based on the determined second entrance blood mass flow rate. In some embodiments, the second exit flow velocity and the second exit blood mass flow rate may be determined in a way similar to the determination of the second entrance flow velocity and the second entrance blood mass flow rate. For example, the second exit flow velocity may be determined based on specific physiological parameters of the subject. Merely for illustration, the second exit flow velocity may be measured non-invasively using a detector (e.g., an ultrasonic detector). The second exit blood mass flow rate may be determined based on the second exit flow velocity. As another example, the processing device 120 may determine the second exit blood mass flow rate based on the first local flow field distribution. The second exit blood mass flow rate may be equal to the first entrance blood mass flow rate. The processing device 120 may further determine the second exit flow velocity based on the determined second exit blood mass flow rate.

In some embodiments, the processing device 120 may determine at least one intermediate blood vessel connecting at least one first blood vessel and at least one second blood vessel. In some embodiments, a flow resistance of each of the at least one intermediate blood vessel may be preset by a user, according to default settings of the imaging system 100, etc. In some embodiments, a flow resistance of each of the at least one intermediate blood vessel may be determined based on the at least one connection model.

The second entrance reference pressure may refer to a reference pressure at the entrance of the at least one second blood vessel. The second exit reference pressure may refer to a reference pressure at the exit of the at least one second blood vessel. In some embodiments, the processing device 120 may determine the second entrance reference pressure based on the first exit reference pressure at the exit of the at least one first blood vessel based on the first local flow field distribution. Merely by way of example, the processing device 120 may determine the second entrance reference pressure according to Equalization (3):

$$P'_i = P_i - R_i Q_i, \quad (3)$$

where $P'_i$ denotes the second entrance reference pressure, $P_i$ denotes the first exit reference pressure at the exit of the at least one first blood vessel, $Q_i$ denotes the first exit blood mass flow rate at the exit of the at least one first blood vessel, $R_i$ denotes the flow resistance of the at least one intermediate blood vessel, and i denotes a count of the at least one intermediate blood vessel. The parameter i may be an integer larger than or equal to 1.

In 812, the processing device 120 (e.g., the flow field determination module 406 or the processor 210) may determine a second local flow field distribution of the meshed second vascular model based on the second boundary condition.

In some embodiments, the processing device 120 may determine the second local flow field distribution of the meshed second vascular model based on the second boundary condition according to a specific algorithm, for example, the CFD algorithm.

In 814, the processing device 120 (e.g., the hemodynamic parameter determination module 408 or the processor 210) may determine at least one of the value of the first hemodynamic parameter of the at least one first blood vessel based on the first local flow field distribution, or the value of the second hemodynamic parameter of the at least one second blood vessel based on the second local flow field distribution.

In some embodiments, the first hemodynamic parameter may include a pressure, a wall stress, a WSS, a flow velocity, or the like, or any combination thereof, at each of one or more positions of the at least a part of the at least one first blood vessel. The second hemodynamic parameter may include a pressure, a wall stress, a WSS, a flow velocity, or the like, or any combination thereof, at each of one or more positions of the at least a part of the at least one second blood vessel. In some embodiments, the determination of the at least one of the value of the first hemodynamic parameter of the at least one first blood vessel or the value of the second hemodynamic parameter of the at least one second blood vessel may be similar to or the same as the operation 508 of the process 500 as illustrated in FIG. 5, the descriptions of which are not repeated here.

According to the embodiments of the process 800, the processing device 120 may determine the first local flow field distribution of the meshed first vascular model based on the first boundary condition. The processing device 120 may also determine the second boundary condition of the second vascular model based on the intermediate model and the first local flow field distribution, and the second local flow field distribution of the meshed second vascular model based on the second boundary condition. The processing device 120 may further determine at least one of the value of the first hemodynamic parameter of the at least one first blood vessel based on the first local flow field distribution, or the value of the second hemodynamic parameter of the at least one second blood vessel based on the second local flow field distribution. By performing the operations exemplified above, the value of the hemodynamic parameter of a blood vessel may be determined in a non-invasive, and the accuracy of the value of the hemodynamic parameter may be effectively improved.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
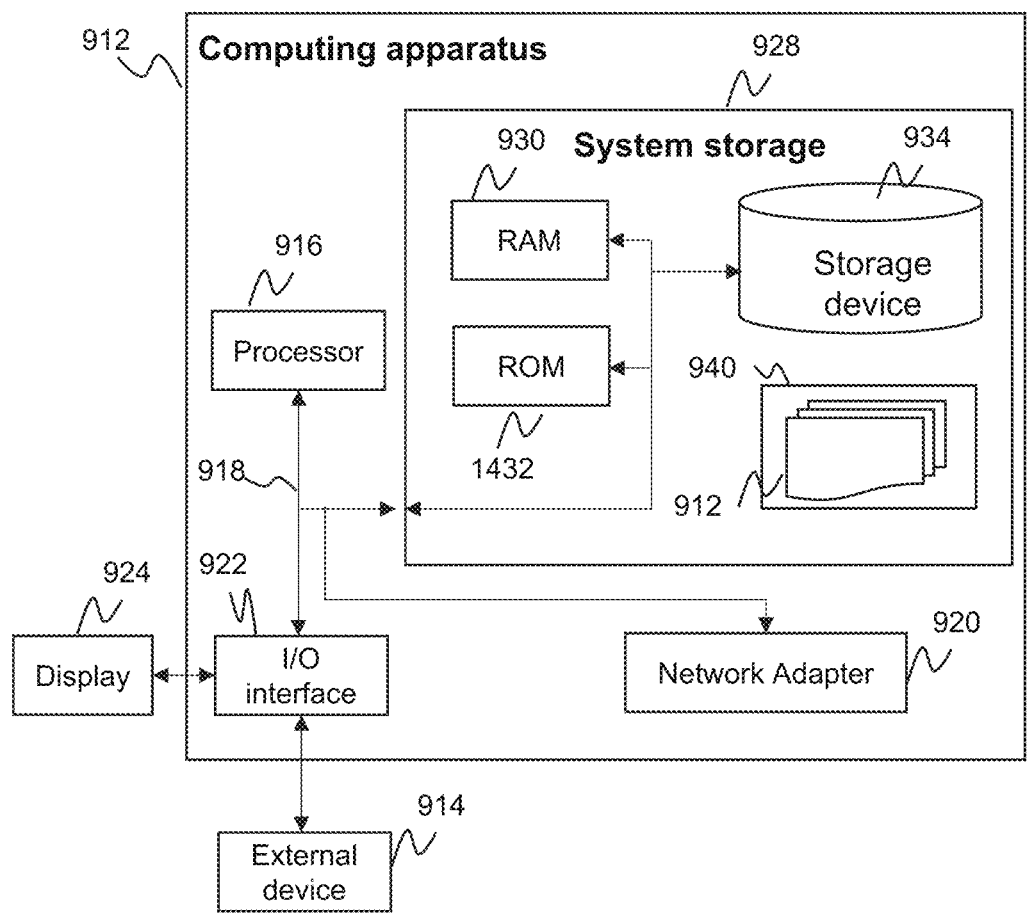
FIG. 9 is a schematic diagram of an exemplary processing device according to some embodiments of the present disclosure.

FIG. 9 is a schematic diagram of an exemplary processing device according to some embodiments of the present disclosure. The computing device 912 may facilitate the implementation of the processes or operations provided in the present disclosure. The computing device 912 illustrated in FIG. 9 is merely an example, but not intended to limit the scope of the present disclosure.

As shown in FIG. 9, the computing device 912 may be implemented by a computing device of general purposes. The computing device 912 may include but are not limited to one or more processors 916, a system memory 928, and a bus 918 that connects elements or components of the computing device 912, such as the system memory 928, the one or more processors 916, etc.

The bus 918 may represent one or more of several types of bus structures, including a memory bus, a memory controller, peripheral bus, an accelerated graphics port, the one or more processors 916, or a local bus using any of a variety of bus structures. For example, the bus structures may include but not limited to, an Industry Standard Architecture (ISA) bus, a Micro Channel Architecture (MAC) bus, an Enhanced ISA Bus, a Video Electronics Standards Association (VESA) local bus, a peripheral component interconnects (PCI) bus, etc.

The computing device 912 may include a variety of computer readable media. The computer readable media may be any available media including volatile or non-volatile media, removable or non-removable media, etc., that may be accessible by the computing device 912.

The system memory 928 may include computer readable media in a form of volatile memory, for example, a random access memory (RAM) 930 and/or a read-only memory (ROM) 932. The computing device 912 may further include other removable/non-removable or volatile/non-volatile computer system storage media. Merely by ways of example, a storage device 934 may be non-removable, non-volatile magnetic media (not shown in the figure, commonly referred to as a "hard disk drive") for reading and writing. Although not shown in FIG. 9, a disk drive for reading and writing to a removable non-volatile disk (such as a "floppy disk") and a removable non-volatile disk (such as a CD-ROM, a DVD-ROM, or other optical media) may be provided. In these cases, each drive may be coupled to the bus 918 via one or more data medium ports. The system memory 928 may include at least one program product having a set (e.g., at least one) of program modules configured to implement the functions provided in the above embodiments of the present disclosure.

A program/utility tool 1440 having a set (at least one) of program modules 1442, which may be stored, for example, in the memory 928. The program modules 1442 may include but not limited to, an operating system, one or more applications, other program modules, or program data. Each or a combination of one or more of the above listed program modules may have a network environment implementation. The program module 1442 may perform the functions and/or methods provided in the described embodiments of the present disclosure.

The computing device 912 may also be in communication with one or more external devices 914 (e.g., a keyboard, a pointing device, a display 924, etc.), one or more devices that enable a user to interact with the computing device 912, and/or any devices (e.g., a network card, a modem, etc.) that enable the computing device 912 to communicate with one or more other computing devices. The communication may be realized via an input/output (I/O) interface 922. Also, the computing device 912 may also communicate with one or more networks (e.g., a local area network (LAN), a wide area network (WAN), and/or a public network, such as the Internet) through a network adapter 920. As shown in the figure, the network adapter 920 may communicate with other modules of computing device 912 via the bus 918. It should be understood that, other hardware and/or software modules may be utilized in combination with the computing device 912, including but not limited to microcode, device drivers, redundant processing units, external disk drive arrays, RAID systems, Tape drives, or data backup storage systems.

The one or more processors 916 may implement, by running a program stored in the system memory 928, various functional applications and/or data processing, for example, a system or method for determining hemodynamic parameters as provided in some embodiments of the present disclosure. According to an aspect of the present disclosure, the method may include generating a first vascular model and a second vascular model based on image data of a subject. The method may include coupling the first vascular model with the second vascular model using an intermediate model to form a coupled vascular model. The method may also include determining a flow field distribution of the coupled vascular model. The method may further include determining a value of a hemodynamic parameter based on the flow field distribution of the coupled vascular model. A hemodynamic parameter of a blood vessel may include a pressure, a wall stress, a wall shear stress (WSS), a flow velocity, etc., at each of one or more positions of the blood vessel. Those skilled in the art may understand that the one or more processors 916 may also implement technical solutions of the exposure process control method provided by any embodiments of the present disclosure.

The present disclosure may further provide a computer readable storage medium storing computer programs. When the computer programs are executed by a processor, operations of classification determination of a structure of a subject in an image provided in the present disclosure may be implemented. According to an aspect of the present disclosure, the operations may include generating a first vascular model and a second vascular model based on image data of a subject. The operations may include coupling the first vascular model with the second vascular model using an intermediate model to form a coupled vascular model. The operations may also include determining a flow field distribution of the coupled vascular model. The operations may further include determining a value of a hemodynamic parameter based on the flow field distribution of the coupled vascular model. A hemodynamic parameter of a blood vessel may include a pressure, a wall stress, a wall shear stress (WSS), a flow velocity, etc., at each of one or more positions of the blood vessel.

It should be noted that the computer programs stored in the computer readable storage medium may not limited to the methods or operations provided above, other methods or operations related to the automated positioning of the subject may also be provided.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution— e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having a processor and a computer-readable storage device, the method comprising:
    obtaining image data of a subject, the subject including at least one first vessel and at least one second vessel, wherein the at least one first vessel and at least one second vessel constitute a blood flow path;
    generating a first vascular model and a second vascular model based on the image data of the subject, wherein the first vascular model and the second vascular model correspond to the at least one first vessel and the at least one second vessel, respectively;
    coupling the first vascular model with the second vascular model using an intermediate model, wherein the first vascular model, the second vascular model, and the intermediate model form a coupled vascular model;
    setting at least one of a first boundary condition of the first vascular model or a second boundary condition of the second vascular model;
    determining a flow field distribution of the coupled vascular model based on the at least one of the first boundary condition of the first vascular model or the second boundary condition of the second vascular model; and
    determining at least one of a value of a first hemodynamic parameter of the at least one first vessel or a value of a second hemodynamic parameter of the at least one second vessel based on the flow field distribution of the coupled vascular model.

2. The method of claim 1, wherein the image data of the subject corresponds to at least two time phases of the subject.

3. The method of claim 1, wherein the generating a first vascular model and a second vascular model based on the image data of the subject includes:
    segmenting the at least one first vessel and at least one second vessel from the image data of the subject;
    extracting features of the segmented at least one first vessel and at least one second vessel; and
    generating the first vascular model and the second vascular model based on the extracted features.

4. The method of claim 1, wherein the first vascular model includes at least one first bifurcation end, and the second vascular model includes at least one second bifurcation end, the coupling the first vascular model with the second vascular model using an intermediate model including:
    determining a correspondence relationship between the at least one first bifurcation end and the at least one second bifurcation end;
    determining one or more bifurcation end pairs based on the correspondence relationship, each of the one or more bifurcation end pairs including a first bifurcation end and a corresponding second bifurcation end; and
    connecting the first bifurcation end and the corresponding second bifurcation end of each of the one or more bifurcation end pairs via a flow resistance model of the intermediate model.

5. The method of claim 4, wherein the flow resistance model is a zero-dimensional model.

6. The method of claim 1, wherein the setting at least one of a first boundary condition of the first vascular model or a second boundary condition of the second vascular model includes:
    setting the first boundary condition of the first vascular model, wherein the first boundary condition includes at least one of a first entrance flow velocity, a first entrance blood mass flow rate, or a first entrance reference pressure at an entrance of the at least one first vessel, or a first exit flow velocity, a first exit blood mass flow rate, or a first exit reference pressure at an exit of the at least one first vessel.

7. The method of claim 6, wherein the determining a flow field distribution of the coupled vascular model based on the at least one of the first boundary condition of the first vascular model or the second boundary condition of the second vascular model includes:
generating a meshed coupled vascular model by gridding the coupled vascular model; and
determining the flow field distribution of the coupled vascular model based on the meshed coupled vascular model and the first boundary condition.

8. A system, comprising:
at least one storage device storing executable instructions, and at least one processor in communication with the at least one storage device, wherein when executing the executable instructions, the at least one processor causes the system to perform operations including:
obtaining image data of a subject, the subject including at least one first vessel and at least one second vessel, wherein the at least one first vessel and at least one second vessel constitute a blood flow path;
generating a first vascular model and a second vascular model based on the image data of the subject, wherein the first vascular model and the second vascular model correspond to the at least one first vessel and the at least one second vessel, respectively;
coupling the first vascular model with the second vascular model using an intermediate model, wherein the first vascular model, the second vascular model, and the intermediate model form a coupled vascular model;
setting at least one of a first boundary condition of the first vascular model or a second boundary condition of the second vascular model;
determining a flow field distribution of the coupled vascular model based on the at least one of the first boundary condition of the first vascular model or the second boundary condition of the second vascular model; and
determining at least one of a value of a first hemodynamic parameter of the at least one first vessel or a value of a second hemodynamic parameter of the at least one second vessel based on the flow field distribution of the coupled vascular model.

9. The system of claim 8, wherein the image data of the subject corresponds to at least two time phases of the subject.

10. The method of claim 8, wherein the generating a first vascular model and a second vascular model based on the image data of the subject includes:
segmenting the at least one first vessel and at least one second vessel from the image data of the subject;
extracting features of the segmented at least one first vessel and at least one second vessel; and
generating the first vascular model and the second vascular model based on the extracted features.

11. The system of claim 8, wherein the first vascular model includes at least one first bifurcation end, and the second vascular model includes at least one second bifurcation end, the coupling the first vascular model with the second vascular model using an intermediate model including:

determining a correspondence relationship between the at least one first bifurcation end and the at least one second bifurcation end;
determining one or more bifurcation end pairs based on the correspondence relationship, each of the one or more bifurcation end pairs including a first bifurcation end and a corresponding second bifurcation end; and
connecting the first bifurcation end and the corresponding second bifurcation end of each of the one or more bifurcation end pairs via a flow resistance model of the intermediate model.

12. The system of claim 11, wherein the flow resistance model is a zero-dimensional model.

13. The system of claim 8, wherein the setting at least one of a first boundary condition of the first vascular model or a second boundary condition of the second vascular model includes:
setting the first boundary condition of the first vascular model, wherein the first boundary condition includes at least one of a first entrance flow velocity, a first entrance blood mass flow rate, or a first entrance reference pressure at an entrance of the at least one first vessel, or a first exit flow velocity, a first exit blood mass flow rate, or a first exit reference pressure at an exit of the at least one first vessel.

14. The system of claim 13, wherein the first entrance flow velocity is measured using an ultrasonic detector.

15. The system of claim 13, wherein the determining a flow field distribution of the coupled vascular model based on the at least one of the first boundary condition of the first vascular model or the second boundary condition of the second vascular model includes:
generating a meshed coupled vascular model by gridding the coupled vascular model; and
determining the flow field distribution of the coupled vascular model based on the meshed coupled vascular model and the first boundary condition.

16. The system of claim 15, wherein the meshed coupled vascular model includes a meshed first vascular model and a meshed second vascular model, the determining the flow field distribution of the coupled vascular model based on the meshed coupled vascular model and the first boundary condition including:
determining a first local flow field distribution of the meshed first vascular model based on the first boundary condition;
determining a second boundary condition of the second vascular model based on the intermediate model and the first local flow field distribution, wherein the second boundary condition includes at least one of a second entrance flow velocity, a second entrance blood mass flow rate, or a second entrance reference pressure at an entrance of the at least one second vessel, or second exit flow velocity, a second exit blood mass flow rate or a second exit reference pressure at an exit of the at least one second vessel; and
determining a second local flow field distribution of the meshed second vascular model based on the second boundary condition.

17. The system of claim 16, wherein the determining at least one of a value of a first hemodynamic parameter of the at least one first vessel or a value of a second hemodynamic parameter of the at least one second vessel based on the flow field distribution of the coupled vascular model includes:
determining at least one of the value of the first hemodynamic parameter of the at least one first vessel based on the first local flow field distribution, or the value of the second hemodynamic parameter of the at least one second vessel based on the second local flow field distribution, the first hemodynamic parameter including at least one of a pressure, a wall stress, a wall shear stress (WSS), or a flow velocity at each of one or more positions of the at least a part of the at least one first vessel, and the second hemodynamic parameter including at least one of a pressure, a wall stress, a WSS, or a flow velocity, at each of one or more positions of the at least a part of the at least one second vessel.

18. The system of claim 8, wherein the at least one first vessel includes a first main vessel and at least one first branch vessel, and the at least one second vessel includes a second main vessel and at least one second branch vessel, the method further including:
  determining a value of a pressure gradient between the first main vessel and the second main vessel.

19. The system of claim 18, wherein the at least one first vessel includes a portal vein, and the at least one second vessel includes a hepatic vein.

20. A non-transitory computer readable medium, comprising at least one set of instructions, wherein when executed by one or more processors of a computing device, the at least one set of instructions causes the computing device to perform a method, the method comprising:
  obtaining image data of a subject, the subject including at least one first vessel and at least one second vessel, wherein the at least one first vessel and at least one second vessel constitute a blood flow path;
  generating a first vascular model and a second vascular model based on the image data of the subject, wherein the first vascular model and the second vascular model correspond to the at least one first vessel and the at least one second vessel, respectively;
  coupling the first vascular model with the second vascular model using an intermediate model, wherein the first vascular model, the second vascular model, and the intermediate model form a coupled vascular model;
  setting at least one of a first boundary condition of the first vascular model or a second boundary condition of the second vascular model;
  determining a flow field distribution of the coupled vascular model based on the at least one of the first boundary condition of the first vascular model or the second boundary condition of the second vascular model; and
determining at least one of a value of a first hemodynamic parameter of the at least one first vessel or a value of a second hemodynamic parameter of the at least one second vessel based on the flow field distribution of the coupled vascular model.

* * * * *